US011488250B2

(12) United States Patent
Conradie et al.

(10) Patent No.: US 11,488,250 B2
(45) Date of Patent: Nov. 1, 2022

(54) USER VERIFICATION BY COMPARING PHYSIOLOGICAL SENSOR DATA WITH PHYSIOLOGICAL DATA DERIVED FROM FACIAL VIDEO

(71) Applicant: LifeQ Global Limited, Dublin (IE)

(72) Inventors: Riaan Conradie, Amsterdam (NL); Etienne Terblanche, Alpharetta, GA (US)

(73) Assignee: LifeQ Global Limited, Dublin (IE)

( * ) Notice: Subject to any disclaimer, the term of this patent is extended or adjusted under 35 U.S.C. 154(b) by 18 days.

(21) Appl. No.: 16/058,668

(22) Filed: Aug. 8, 2018

(65) Prior Publication Data

US 2019/0050943 A1 Feb. 14, 2019

Related U.S. Application Data

(60) Provisional application No. 62/543,779, filed on Aug. 10, 2017.

(51) Int. Cl.
*G06Q 40/08* (2012.01)
*G06Q 30/00* (2012.01)
(Continued)

(52) U.S. Cl.
CPC ......... *G06Q 40/08* (2013.01); *G06Q 30/0185* (2013.01); *G06V 30/418* (2022.01);
(Continued)

(58) Field of Classification Search
CPC .......... A61B 2576/023; A61B 5/02405; A61B 5/02416; A61B 5/02438; A61B 5/0261;
(Continued)

(56) References Cited

U.S. PATENT DOCUMENTS 9,769,368 B1 * 9/2017 Morford ............ H04N 5/23225
2003/0200217 A1 * 10/2003 Ackerman ............ G06Q 30/06
(Continued)

FOREIGN PATENT DOCUMENTS

| KR | 20070025451 A | * | 3/2007 |
|---|---|---|---|
| TW | 201721509 | | 6/2017 |
| WO | WO20170132061 | | 8/2017 |

OTHER PUBLICATIONS

The Extended European Search Report released by the European Patent Office dated Apr. 7, 2021 for corresponding European Patent Application No. EP188448153; 7 pages.
(Continued)

*Primary Examiner* — Joseph W. King
*Assistant Examiner* — Divesh Patel
(74) *Attorney, Agent, or Firm* — Smith Gambrell & Russell LLP

(57) ABSTRACT

To participate in a health incentive program, a customer of a health-related business such as a health insurance company or medical group entity may use a physiological measurement device to report health-related activity to the business. However, a customer may report fraudulent activity to the business by allowing another party to use the physiological measurement device. In embodiments, an electronic device, a collection and validation server, and a physiological measurement device may execute methods to ensure that the user of the physiological measurement device has identified themselves properly to the business. In embodiments, the electronic device and the physiological measurement device may produce sets of physiological measurement data that are compared to determine that a user of the electronic device is the same as the user of the physiological measurement device. The electronic device may produce a set of physi-
(Continued)

ological measurement data using video and image processing techniques.

19 Claims, 12 Drawing Sheets

(51) Int. Cl.
G06V 30/418 (2022.01)
G06V 40/16 (2022.01)
G06V 40/40 (2022.01)
G06V 40/70 (2022.01)
G06V 40/10 (2022.01)
A61B 5/00 (2006.01)
A61B 5/1171 (2016.01)
G06Q 30/02 (2012.01)

(52) U.S. Cl.
CPC .......... *G06V 40/168* (2022.01); *G06V 40/172* (2022.01); *G06V 40/40* (2022.01); *G06V 40/70* (2022.01); *G06V 40/15* (2022.01)

(58) Field of Classification Search
CPC ... A61B 5/0295; A61B 5/6898; A61B 5/7246; A61B 5/7264; A61B 5/7275; A61B 5/7282; G06Q 40/08; G06Q 40/00; G06Q 30/0185; G06K 9/00268; G06K 9/00288; G06K 9/00483; G06K 9/00892; G06K 2009/00939; G06K 9/00899
USPC .......................................................... 705/4
See application file for complete search history.

(56) References Cited

U.S. PATENT DOCUMENTS

| | | | | |
|---|---|---|---|---|
| 2004/0077934 A1* | 4/2004 | Massad | ............... | A61B 5/0205 600/300 |
| 2004/0101178 A1* | 5/2004 | Fedorovskaya | .......... | H04N 1/32 382/128 |
| 2004/0116784 A1* | 6/2004 | Gavish | ............... | A61B 5/14551 600/300 |
| 2004/0162035 A1* | 8/2004 | Petersen | ............... | A61B 5/1112 455/90.1 |
| 2004/0162466 A1* | 8/2004 | Quy | ........................ | G16H 70/60 600/300 |
| 2004/0193026 A1* | 9/2004 | Scharf | ................. | A61B 5/14551 600/323 |
| 2004/0242973 A1* | 12/2004 | Tanabe | .................. | G16H 40/67 600/300 |
| 2004/0243443 A1* | 12/2004 | Asano | ................... | G06Q 10/10 705/2 |
| 2005/0038326 A1* | 2/2005 | Mathur | ............... | G08B 21/0247 600/300 |
| 2005/0075542 A1* | 4/2005 | Goldreich | ............ | A61B 5/6887 600/300 |
| 2011/0001605 A1* | 1/2011 | Kiani | ..................... | G16H 30/20 340/5.6 |
| 2011/0213700 A1* | 9/2011 | Sant'Anselmo | ....... | G06Q 20/10 705/39 |
| 2011/0276423 A1* | 11/2011 | Davidson | ........... | G06Q 30/0601 705/26.1 |
| 2011/0307403 A1* | 12/2011 | Rostampour | ........ | G06Q 50/265 705/325 |
| 2012/0059911 A1* | 3/2012 | Randhawa | ............. | G16H 40/67 709/219 |
| 2013/0215116 A1* | 8/2013 | Siddique | .............. | G06Q 20/204 345/420 |
| 2013/0332286 A1 | 12/2013 | Medellus et al. | | |
| 2014/0139616 A1* | 5/2014 | Pinter | ................. | A61B 5/02055 348/14.08 |
| 2014/0200416 A1* | 7/2014 | Kashef | ................... | G16H 40/67 600/301 |
| 2014/0294257 A1* | 10/2014 | Tussy | ..................... | G06Q 10/00 382/118 |
| 2014/0316220 A1 | 10/2014 | Sheldon | | |
| 2014/0337093 A1* | 11/2014 | Jain | ....................... | H04L 67/306 705/7.29 |
| 2014/0378810 A1* | 12/2014 | Davis | .................. | A61B 5/1034 600/407 |
| 2015/0035643 A1 | 2/2015 | Kursun | | |
| 2015/0095352 A1* | 4/2015 | Lacey | .................. | G06Q 20/389 707/752 |
| 2015/0126875 A1* | 5/2015 | Poh | ...................... | A61B 5/7264 600/479 |
| 2016/0001781 A1* | 1/2016 | Fung | ..................... | G16H 50/20 701/36 |
| 2016/0162729 A1* | 6/2016 | Hagen | .................. | G06V 40/161 382/118 |
| 2016/0180150 A1 | 6/2016 | Negi et al. | | |
| 2016/0205096 A1 | 7/2016 | Hoyos et al. | | |
| 2016/0210602 A1* | 7/2016 | Siddique | ........... | G06Q 30/0601 |
| 2016/0232534 A1* | 8/2016 | Lacey | ................ | G06Q 20/4016 |
| 2016/0283787 A1 | 9/2016 | Nepomniachtchi et al. | | |
| 2016/0381013 A1* | 12/2016 | Buscemi | ................ | H04L 63/10 726/4 |
| 2017/0109819 A1 | 4/2017 | Amtrup et al. | | |
| 2017/0119258 A1* | 5/2017 | Kotanko | ............... | G06T 7/0016 |
| 2017/0140128 A1* | 5/2017 | Pathangay | .............. | G06F 1/324 |
| 2017/0140174 A1* | 5/2017 | Lacey | ................. | G06F 21/6245 |
| 2017/0156608 A1* | 6/2017 | Mahar | .................. | A61B 5/0205 |
| 2017/0232300 A1* | 8/2017 | Tran | ........................ | G16H 20/30 434/247 |
| 2017/0269132 A1* | 9/2017 | Ambrosio | ............ | G01R 15/207 |
| 2018/0235468 A1* | 8/2018 | Khachaturian | ....... | G06F 1/1632 |
| 2019/0019184 A1* | 1/2019 | Lacey | ................ | G06Q 20/4016 |

OTHER PUBLICATIONS

Meng, Weizhi et al., "Surveying the Development of Biometric User Authentication on Mobile Phones" IEEE Communications Surveys & Tutorials, vol. 17, No. 3, pp. 1268-1293; Dec. 31, 2014.

Arteaga-Falconi, Juan et al., "ECG Authentication for Mobile Devices" IEEE Transactions on Instrumentation and Measurement, vol. 65, No. 3, pp. 591-600; Mar. 1, 2016.

The first Office Action released by the Taiwan Patent Office dated Mar. 3, 2022 for corresponding Taiwan Patent Application No. 107127875; 11 pages.

* cited by examiner

USER VERIFICATION BY COMPARING PHYSIOLOGICAL SENSOR DATA WITH PHYSIOLOGICAL DATA DERIVED FROM FACIAL VIDEO

CROSS-REFERENCE TO RELATED APPLICATIONS

The present application claims the benefit of U.S. Provisional Appl. No. 62/543,779, filed Aug. 10, 2017, which is incorporated by reference herein in its entirety.

FIELD

The disclosure relates to physiological data collected by physiological sensors and video-based methods, and specifically towards user verification based on those different data sources.

BACKGROUND

Physiological measurement devices have become a ubiquitous piece of technology for modern living. Physiological measurement devices contain one or many physiological sensors that collect data that can be used to monitor the health of the user—number of steps walked, temperature, blood pressure, blood-sugar level, heart rate, etc. These technologies allow people to track their general health and track progress towards their health goals. According to International Data Corporation, 102.4 million physiological measurement devices were shipped in 2016. Many devices are designed specifically for health and fitness related monitoring as compared to more general "smartwatch" technologies. Such devices include, for example, fitness bands, smart watches, "smart" weight scales, blood pressure cuffs, and other wearable and non-wearable sensors for obtaining a user's physiological data.

Physiological measurement devices can generally be paired with electronic devices via well-known radio technologies such as Bluetooth and WiFi. This is necessary due to the small-form factor of the physiological measurement devices, which limits the amount of computing and memory resources the device has available. By pairing with a more complex device such as a smartphone or laptop computer, more complex operations and statistics as well as long-term storage can be implemented for the data generated by the physiological sensors on the physiological measurement device. For example, a user of such technology may jog every day, and either during or after each jog the physiological measurement device may send all data collected to the more complex device, to allow the more complex device to store and perform interesting health statistics based on the data.

Insurance companies, for example, have recently shown interest in using such technologies to monitor the health of their insurees. Insurers have a particular interest in keeping their insurees healthy—these insurees are less likely to require significant health expenditure that would be covered by insurers. Thus, several insurers have begun to offer incentives to allow the insurers to monitor the health of their insurees. This may allow the insurers to proactively remind their insurees of health tips specific to their physiological conditions.

Furthermore, insurers may also offer incentives to their insurees to encourage a healthy lifestyle. For example, an insurer may offer a discount on an insuree's premium or offer some form of monetary gift if the user walks 10,000 steps a day, which can be monitored via a step counter using gyroscopes and motion sensors on the physiological measurement device, or engages in cardio exercise for some total amount of time every week, which can be monitored by a heart rate monitor on the device. This is beneficial for both parties—an insurer can reduce the risk of an insuree requiring an insurance payout in the future while still collecting premium fees, and the insuree can save money and improve their health.

However, this incentive system has also created a market for fraudulent behavior. Unscrupulous insurees may game the incentive structure by simply placing their device on another entity, such as an active pet or a health-conscious friend, so that the data collected is actually a result of activity of the other entity rather than the insuree. This would allow the insuree to collect incentive rewards for healthy activity performed by the other entity. Therefore, methods and systems need to be designed to verify that the user of a physiological device is in fact the insuree, and not another entity.

SUMMARY

Systems and methods are described for verifying the identity of a user of a physiological measurement device to prevent fraudulent activity in a health incentive program. In embodiments, a collection and validation server, a physiological measurement device, and an electronic device such as a smartphone perform several steps to verify that a person that wishes to participate in a health incentive program offered by a third party is a customer of that third party (e.g. an insuree of an insurance company, or a patient of a medical group entity such as a health management organization), and that the person using the physiological measurement device is the same as that customer.

In an embodiment, a user of an electronic device captures an image of an identity document with the electronic device. For example, a smartphone may be used to take a picture of an identity document such as a driver's license or passport. The photo is sent to the collection and validation server, and the server processes the identity document to obtain legal information about the user and facial feature information from the photo on the identity document using facial recognition techniques. The legal information is used to determine if the owner of the identity document is a customer of the third party, and the facial feature information is stored for later user verification procedures. In another embodiment, the user may take a "selfie" photo of their face and send this photo to the collection and validation server. The collection and validation server may then obtain facial feature information by performing facial recognition on the selfie photo, and determine if this facial feature information matches the facial feature information of the identity document photo. The collection and validation server can then determine whether or not the current user of the electronic device is the same as the customer of the third party.

In another embodiment, the electronic device receives a set of heart measurements from the physiological measurement device that is purportedly being worn by the user of the electronic device. The electronic device simultaneously records video of the face of the user of the electronic device, and generates a set of video-based heart measurements by image processing the video. In one embodiment, Eulerian Video Magnification is used to detect subtle variations in the skin color of the user's face when a heart beats. These heart rate measurements are sent to the collection and validation server for comparison, at which point it can be determined whether or not the user of the physiological measurement device is the same as the user of the electronic device, the user of the electronic device having already been confirmed to be a customer of the third party offering the health incentive program.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 8A:
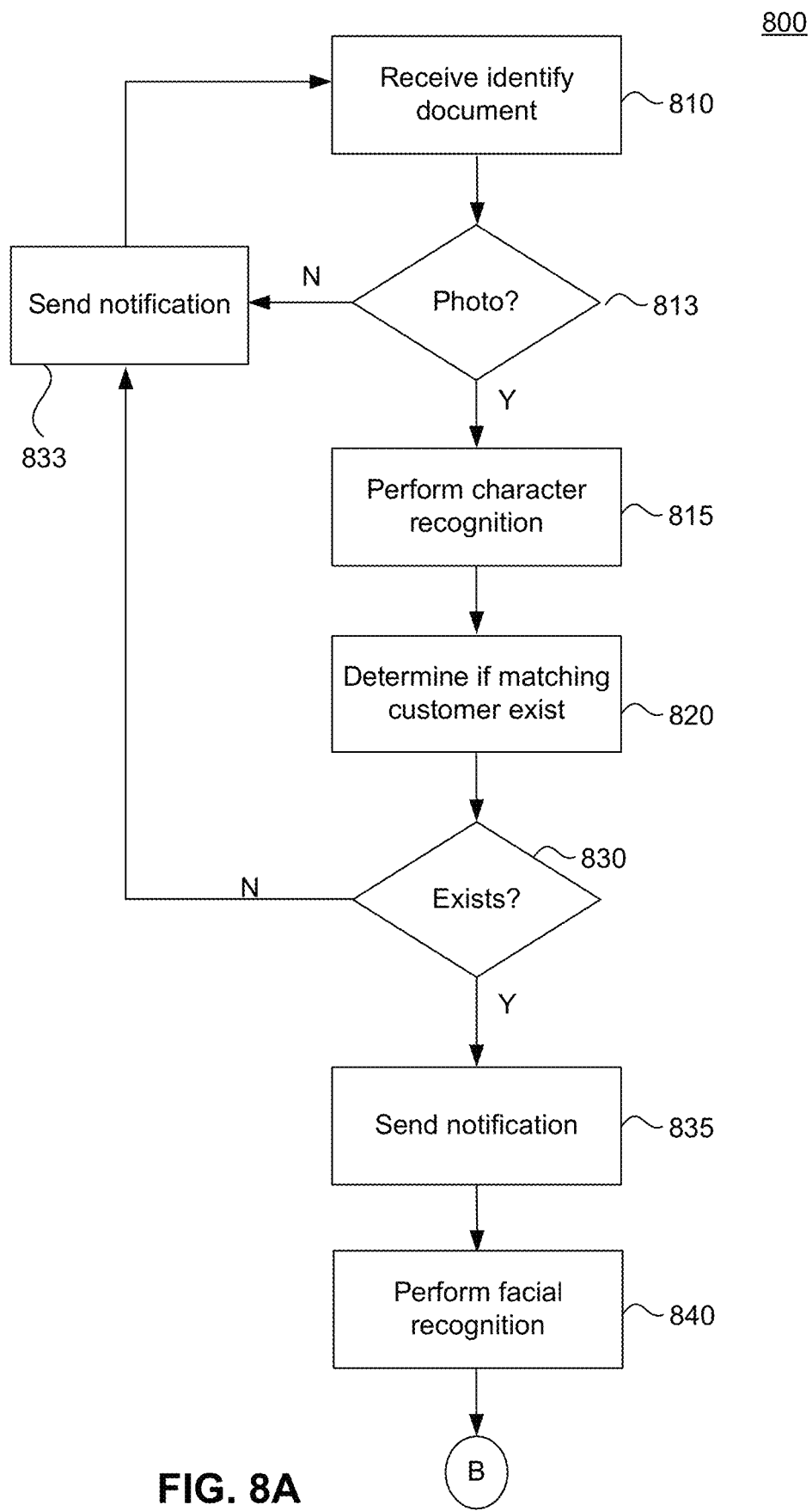
Figure 8B:
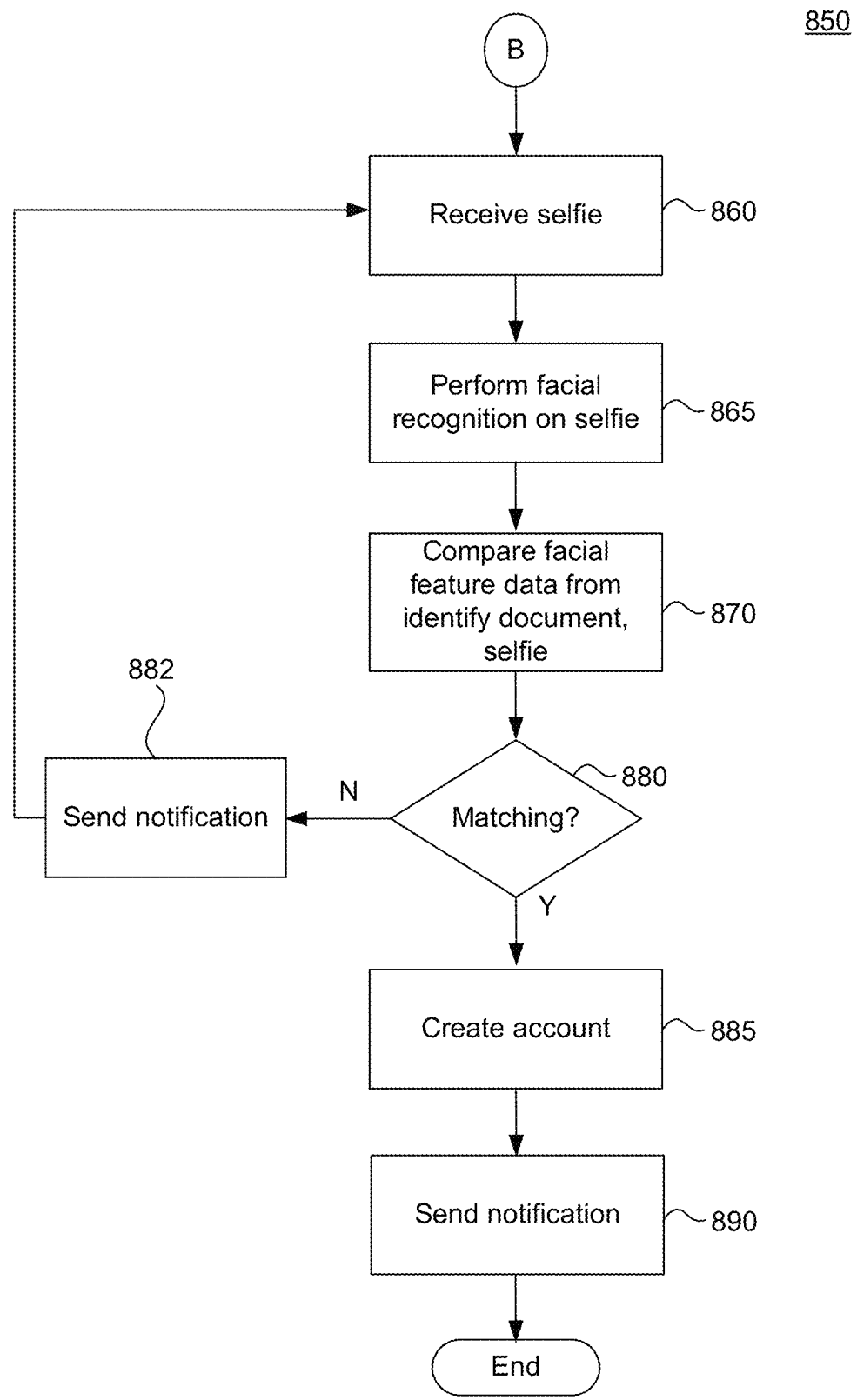

FIGS. 8A-B illustrate flowcharts for identity verification according to embodiments.

Figure 9:
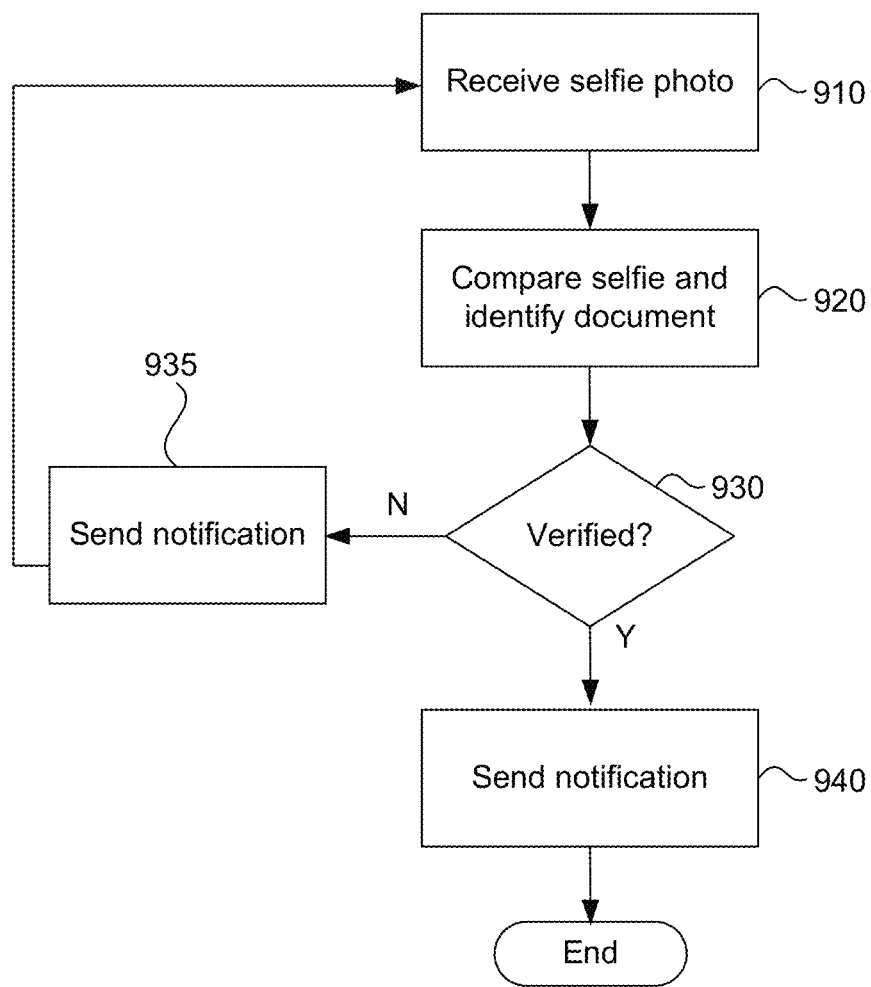

FIG. 9 illustrates another flowchart for user verification according to an embodiment.

Figure 10:
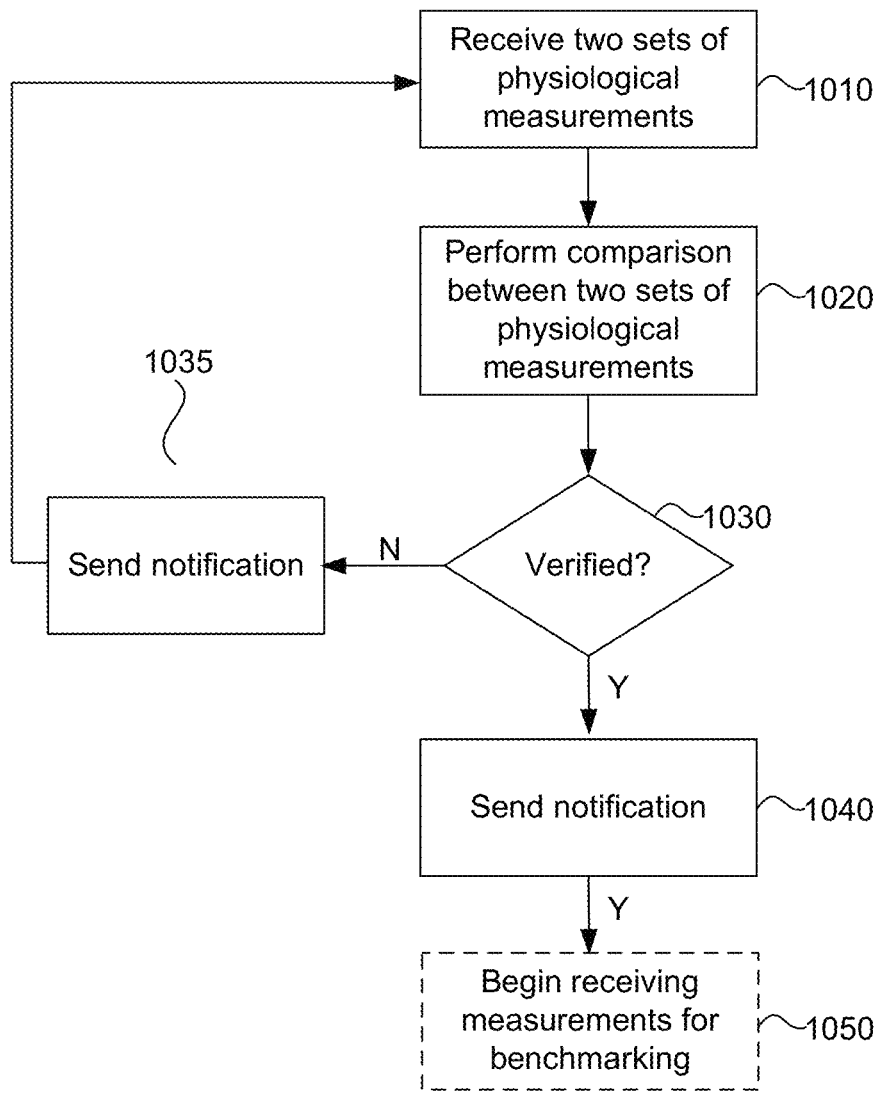

FIG. 10 illustrates another flowchart for user data collection and verification according to an embodiment.

Figure 11:
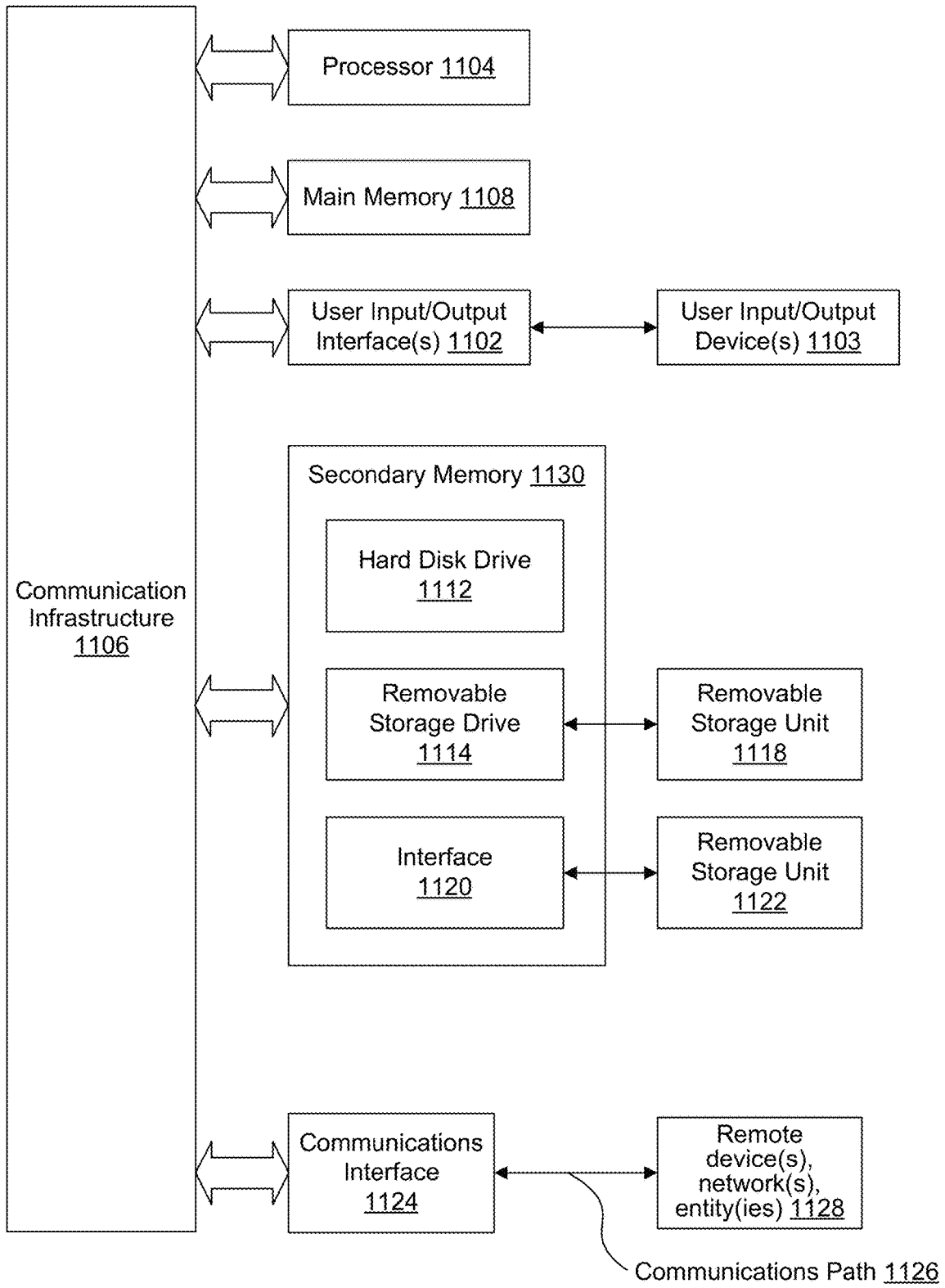

FIG. 11 illustrates a computer system, according to example embodiments of the present disclosure.

The present disclosure will be described with reference to the accompanying drawings. In the drawings, like reference numbers indicate identical or functionally similar modules.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" shall be understood to include at least one of software, firmware, and hardware (such as one or more circuit, microchip, or device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner.

The following detailed description of the exemplary embodiments will so fully reveal the general nature of the disclosure that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

The disclosure is organized as follows. First, the overall system and the different devices involved in the user verification are described. Second, methods for user verification related to a user's devices are described, the devices including a physiological sensor and an electronic device. Third, methods for user verification related to a collection and validation server are described, where the collection and validation server may be implemented as one or more cloud services. Finally, a computer system is described that may implement aspects of the system.

System and Devices for User Verification

Figure 1:
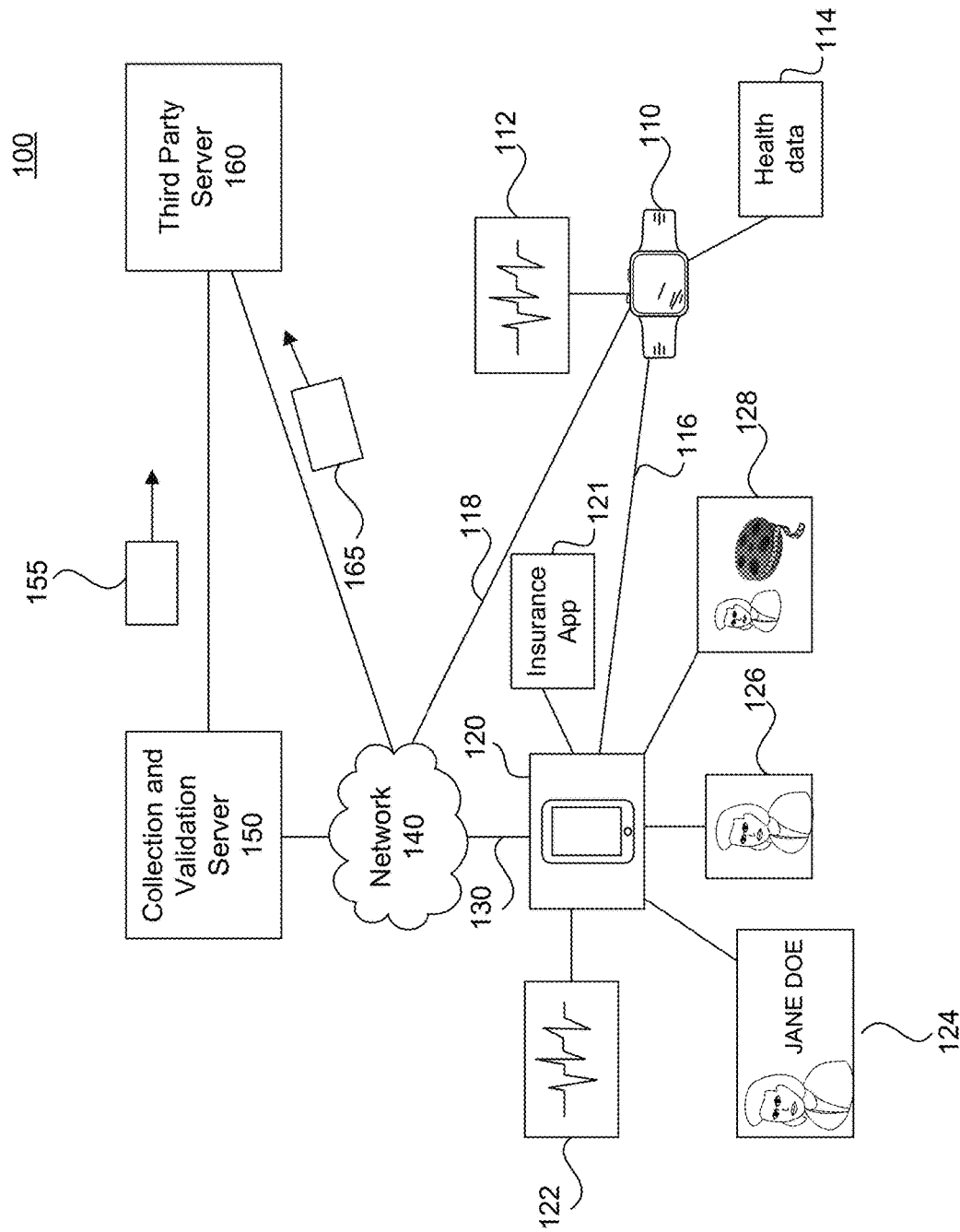
FIG. 1 illustrates a diagram of a system for user verification of a physiological sensor according to an embodiment.

FIG. 1 shows a system 100 for collecting physiological data and performing user verification for a user of a physiological measurement device. System 100 includes several devices including physiological measurement device 110, electronic device 120, network 140, collection and validation (CV) server 150, and a third party server 160. In embodiments, electronic device 120 may be a smartphone, a tablet computer, or another computing device. CV server 150 and third party server 160 may each be implemented as one or more server devices, or virtually as a cloud service. In an embodiment, physiological measurement device 110 and electronic device 120 are carried by the user of the devices, CV server 150 is owned or provided by a party that receives data for verifying the identity of the user, and third party server 160 is owned or provided by an interested third party such as a medical group entity or an insurance company that wishes to receive physiological data from the user while ensuring the data's validity by receiving information from CV server 150.

In embodiments, the third party may offer a health incentive program in which the user can participate by reporting health data to the third party, either directly or via CV server 150. Each of these parties may perform aspects of user data collection and user verification to ensure that the user of physiological measurement device 110 is the same individual that the interested third party believes it is. The different entities work in tandem to ensure that the user of physiological measurement device 110 is the same as a customer of the interested third party, such that the physiological data reported from physiological measurement device 110 truly reflects the physical condition of a customer of the interested third party and not an impersonating party.

Each of the devices in system 100 may collect various data about the user, either directly from the user or through other devices within system 100. In an embodiment, physiological measurement device 110 specifically collects various health data 114 of a user of physiological measurement device 110, such as number of number of steps walked in a session, blood pressure, blood-sugar levels, and myriad other data that medical professionals may use as indicators of the general health of the user of physiological measurement device 110. For the purposes of verification (in addition to indicating general health), physiological measurement device 110 also collects physiological measurement data 112. In an embodiment this physiological measurement data may be a simple heart rate value such as beats per minute (BPM), that is calculated by counting the number of pulses over an amount of time and then normalizing over that amount of time. The BPM can then be recalculated several times for numerous overlapping time windows. For example, a BPM may be calculated over thirty-second windows with a fifteen-second overlap, so that from an initial starting time of 0 s, a BPM may be calculated based on the number of heart beats from 0 s to 30 s, 15 s to 45 s, 30 s to 60 s, and so on.

In another embodiment, the heart rate information may in fact mark timestamps for each individual beat, and store all of the timestamps for later processing. Many physiological measurement devices may be capable of obtaining timestamps on the order of tens of milliseconds or millisecond accuracy, thus allowing for very accurate timestamps. Thus, a string of decimal values may be stored in a memory of physiological measurement device 110, such as 12:01:01.0000, 12:01:01.9895, 12:01:02.9786, 12:01:03.9683, and so on, and output to another device for further processing.

While various embodiments described herein refer to physiological measurements or information, a person of skill in the art will recognize that many types of physiological measurements, such as heart rate, RR intervals, pulse waveform measurement, or any other physiological measurement, may be used.

Health data 114 and physiological measurement data 112 may be sent via link 116 to electronic device 120. In an embodiment, link 116 is a wireless link employing a standard protocol such as one of the many Bluetooth protocols. Bluetooth is common because it provides a bandwidth that is appropriate to the size of health data 114 and physiological measurement data 112, has a point-to-point wireless connection, and has a low power requirement, thereby not draining the energy resources of physiological measurement device 110 too significantly.

As was described, electronic device 120 collects health data 114 and physiological measurement data 112 from physiological measurement device 110 via link 116. In an embodiment, this data can be stored long-term within electronic device 120 and output to another device owned by the user, such as a laptop or computer. It can also be sent to CV server 150 and third party server 160 via network 140, which connects to electronic device 120 via link 130. In embodiments, link 130 may be a wireless link such as a IEEE 802.11 "WiFi" link from one of several standards, or a cellular link such as an 4G Long-Term Evolution (LTE), WiMAX, 3G Universal Mobile Telecommunications System (UMTS), code division multiple access (CDMA), or other standard employed by a cellular telecommunications carrier to serve electronic devices such as electronic device 120. In embodiments, the network 140 may consist of several switch, router, and server devices common in typical network implementations. These devices may be comprised of commonly accessible Internet devices and dedicated network resources such as those used by a cellular telecommunications carrier.

Electronic device 120 may host application 121 that works in conjunction with CV server 150 to perform user verification, to ensure that the user of physiological measurement device 110 is the same as a customer of the third party. Application 121 may prompt the user of electronic device 120 for inputs to verify his or her identity with CV server 150 and third party server 150. In embodiments, application 121 may prompt the user of electronic device 120 for identity document photo 124, photo 126 (otherwise known as a "selfie"), and video 128. In embodiments, video 128 may be a continuous video of the face of the user of electronic device 120.

Thus, electronic device 120 collects several pieces of information to aid in the verification of the user of physiological measurement device 110. Electronic device 120 may prompt the user of electronic device 120 via application 121 to take a photo of identity document photo 124. Identity document photo 124 may be one of many legally recognized photo identification documents, such as a passport, state-issued ID, or driver's license. In an embodiment, identity document photo 124 contains both legal information as well as a photo of the user. This documentation can be used by CV server 150 as well as third party server 160 to determine the appearance of a person via facial recognition algorithms, and match it to a name of a customer of the owner of the third party server. In addition, CV server 150 and third party server 160 may use optical character recognition (OCR) techniques to determine the text in the identity document to ensure that the legal information such as name, date of birth, and identification or driver's license number of the user matches a customer of the third party. In an embodiment, the photo contained in identity document photo 124 may also serve as a baseline photo for comparison to a user of physiological measurement device 110 using facial recognition. This process will be described in more detail below.

In an embodiment, electronic device 120 may prompt the user of electronic device 120 via application 121 to take a "selfie" photo 126 of their own face. Electronic device 120 may then send photo 126 to CV server 150 to compare to the photo in identity document photo 124. This may allow CV server 150 to determine that the user in possession of electronic device 120 is the same as the person in identity document photo 124 using facial recognition techniques. In various embodiments to be described below, the user may be prompted to take a new photo 126 of his or her own face as part of the process for user verification.

In an embodiment, electronic device 120 may also request, via application 121, for the user to film video 128 of their own face for a short period of time. In an embodiment, the user's face must be within the viewable area of the video for some continuous amount of time. If not, electronic device 120 may cease filming and send a new request via application 121 for the user to film video of his or her own face. In an embodiment, photo 126 may also be obtained as a single frame from within video 128, either during or after video 128 has completed filming. Video 128 may contain metadata of timing information to allow electronic device 120 to determine the exact time that a given frame of video 128 was shot, on the order of tens of milliseconds or millisecond accuracy. In an embodiment, video 128 may not be required to be directed to the face of the user but instead on some other body part of the user.

In an embodiment, electronic device 120 may determine video-based physiological measurement data 122 based on video 128. Several techniques now exist to detect, for example, the time of a heartbeat pulse of a person appearing in a video. One such technique, Eulerian Video Magnification, amplifies the changes in color variation in the video. This technique takes advantage of the fact that a color variation occurs on a person's skin when the person's heart beats, a variation that is imperceptible to the human eye but observable through image processing of video frames. Using such techniques, electronic device 120 may determine video-based physiological measurement data 122. In embodiments, video-based physiological measurement data 122 may be of similar format to physiological measurement data 112 generated by physiological measurement device 110. In an embodiment, video-based physiological measurement data 122 may be a beats per minute measurement generated for overlapping time windows as described above relative to physiological measurement data 112. In another embodiment, video-based physiological measurement data 122 may be a series of timestamps that indicate a time of a heart beat pulse with tens of milliseconds or millisecond accuracy, as described above relative to physiological measurement data 112.

In embodiments, some combination of physiological measurement data 112, video-based physiological measurement data 122, health data 114, photo 126, and identity document photo 124 may be sent from electronic device 120 to CV server 150. In another embodiment, video 128 may also be sent to CV server 150. CV server 150 may use this data to perform user verification to ensure that the user of physiological measurement device 110 is the same as the user of electronic device 120, and that this user is the same as a customer of the third party that owns third party server 160. The processes by which CV server 150 performs such validation will be described in greater detail below.

CV server 150, after performing user verification, may send data 155 to third party server 160 indicating that a user has been verified. This data may include any of the data sent from electronic device 120 to CV server 150, as well as metadata that is generated by CV server 150 when it processes that data from electronic device 120. For example, the name, date of birth, and facial recognition metadata may be sent from CV server 150 to third party server 160. In addition, data 155 may include ongoing data indicating the probability that health data 114 being received by third party server 160 is being generated fraudulently. This is based on health data 114 being compared to benchmark data that is generated by the system when a user first registers with the system to provide health data to the owner of third party server 160. In embodiments, a comparison between health data 114 and the benchmark data stored at CV server 150 may be used to determine the probability that health data 114 is fraudulent, where the comparison is performed using many machine-learning and statistical techniques.

In embodiments, third party server 160 may receive data 155 from CV server 150, and may also receive data 165 directly from electronic device 120 via network 140. For example, after user verification has been completed, health data 114 may be sent directly to third party server 160 from electronic device 120, while data 155 may be generated by CV server in tandem and sent to third party server 160. In another embodiment, electronic device 120 may only send data to CV server 150, at which point CV server 150 may send any necessary data to third party server depending on service level agreements business agreements between the provider of CV server 150 and the user verification service and the owner of third party server 160.

Figure 2:
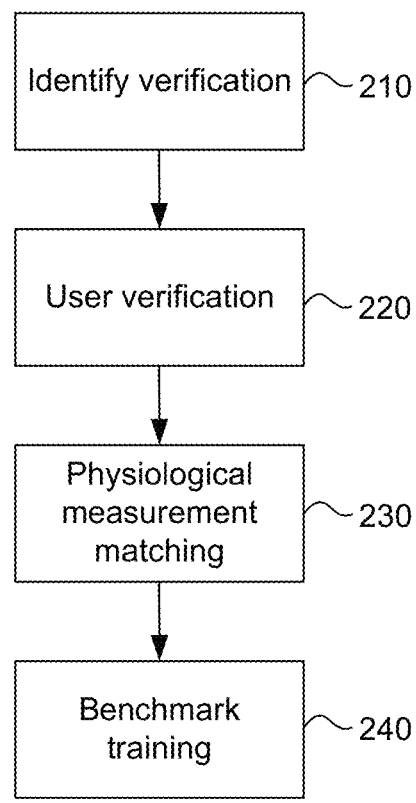
FIG. 2 illustrates a flowchart for the different processes for user identification according to an embodiment.

FIG. 2 illustrates a flowchart 200 of the different user verification processes that may be performed by the elements of system 100, according to an embodiment. The first step of flowchart 200 is identity verification step 210. In identity verification step 210, a user of an electronic device, such as electronic device 120, may take a photo of an identity document, such as identity document 124, to send to a CV server such as CV server 150. The photo of this document will then be scanned using text recognition on the text of the document, to determine if the identity document matches a person with an account associated with the third party owning third party server 160, to determine if the user of the electronic device is indeed a customer of the third party server owner, such as an insuree or a medical patient of an insurance company or medical group entity. The photo may also be scanned using facial recognition on the photo of the person within the identity document, and the facial feature information created from the facial recognition will be stored for later user verification steps.

In this phase, the user of the electronic device may also be instructed to take a photo of himself or herself, i.e. a "selfie", to ensure that the user of the phone is indeed the same as the person depicted in the identity document photo. Facial recognition may be used, wherein facial feature information is extracted based on the selfie photo and compared to the facial feature information extracted from the identity document photo to determine if the person using the electronic device and the person in the identity document are the same person. If it is so determined, and the identity document data has been verified to correspond to a customer of the third party, an account may be generated that associates the identity document information, the facial feature from the identity document, and the electronic device itself with the customer. At this point, the user of the electronic device, who is a customer of the third party, may take part in a health incentive program offered by the third party. During this step, a physiological measurement device such as physiological measurement device 110 may also be associated with the account.

Following identity verification step 210, when the user of the electronic device wishes to send health data to the third party to engage in the health incentive program, a user may be asked to initiate user verification step 220. This step is essentially an abridged form of the identity verification step 210. In step 220, the user of an electronic device such as electronic device 120 may be asked to send a selfie photo of him or herself to the CV server, such as CV server 150, to be compared against the facial feature information of the identity document that was obtained in identity verification step 210. This step may be required immediately prior to the user of the electronic device any time that the user wishes to report health data to the third party.

Before the user of the electronic device can begin participating in the health incentive program, the user may also be asked to perform a physiological measurement matching step 230 and a benchmark training step 240. The physiological measurement data matched in step 230 may be, for example, heart rate data or other types of physiological measurements, such as RR intervals or pulse waveform measurements. In physiological measurement matching step 230, the user of the electronic device may be asked to activate the physiological measurement device that the user wishes to use to send health data to the third party. To prevent fraud at this point, measures must be taken to ensure that the user of the electronic device and the user of the physiological measurement device are indeed the same person. This is achieved by way of physiological measurement matching step 230. During this step, physiological measurement data, such as physiological measurement data 112, is generated by the physiological measurement device, and a second set of video-based physiological measurement data, such as video-based physiological measurement data 122, is generated by the electronic device completely independent from the physiological measurement data from the physiological measurement device. Both forms of physiological measurement data are generated simultaneously and sent to a CV server, such as CV server 150, to determine if they are both generated from the same person. If they are, benchmark training step 240 may commence.

Benchmark training step 240 occurs immediately following a successful outcome from physiological measurement matching step 230, where the user of the electronic device and the physiological measurement device, now determined to be the same user, is instructed to continuously wear the physiological measurement device for some extended period of time. Health data, such as health data 114, is continuously collected from the physiological measurement device during this time. This allows statistical and machine learning models to be generated from the data that reflect the general health and behavior of the user, such as resting heart rate, blood pressure, and blood sugar level, as well as common times for cardiovascular exercise, sleep, and so on. At subsequent sessions when the physiological measurement device sends data purportedly reflecting activity by the customer of the third party, this data can be compared against the models determined in benchmark training step 240 to determine the probability that the data accurately reflects activity by that customer.

Figure 3:
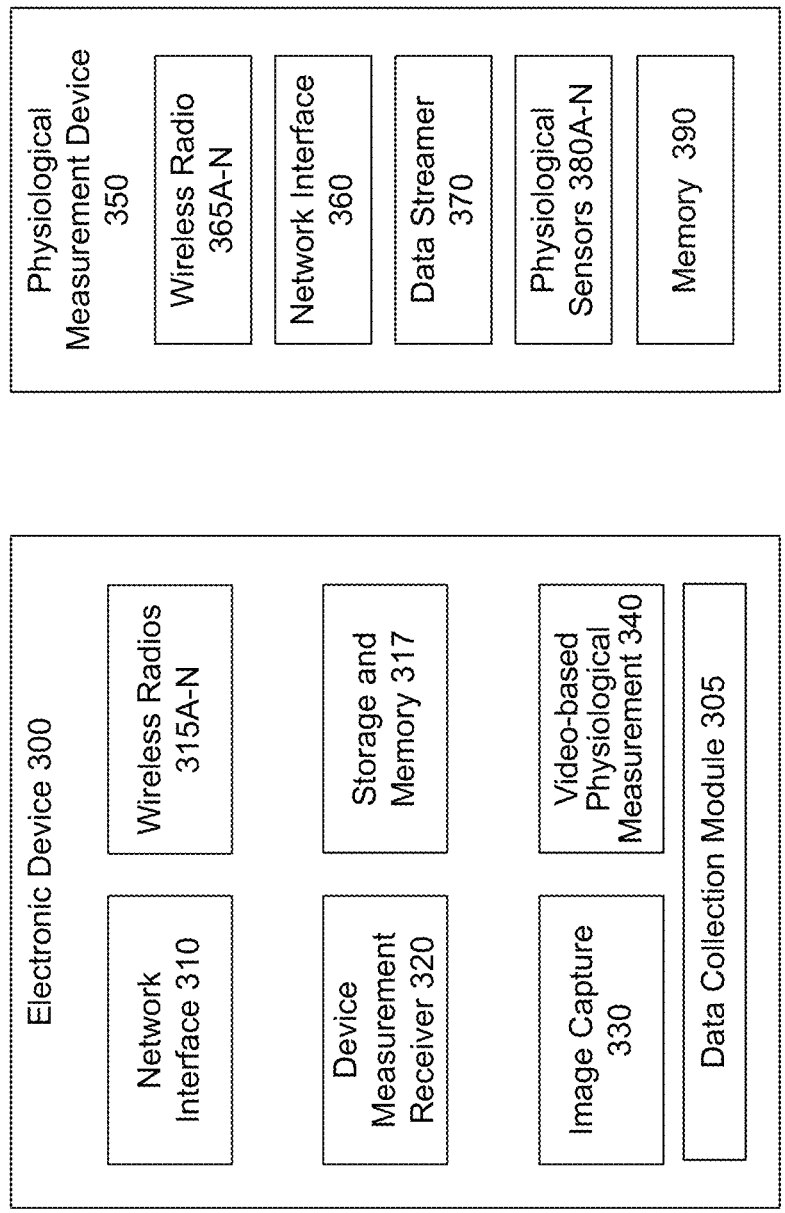
FIG. 3 illustrates a block diagram of user devices according to embodiments.

FIG. 3 illustrates electronic device 300 and physiological measurement device 350 according to an embodiment. The elements of electronic device 300 and physiological measurement device 350 embody all of the features used to perform verification, and are not meant to be limiting. In an embodiment, both electronic device 300 and physiological measurement device 350 are associated with a customer of the owner of a third party server, such as third party server 160. The owner may be an insurance company or a medical group entity. Electronic device 300 may be an embodiment of electronic device 120 depicted in FIG. 1, while physiological measurement device 350 may be an embodiment of physiological measurement device 110 of FIG. 1. Electronic device 300 comprises a network interface 310, wireless radios 315*a-n*, storage and memory 317, device measurement receiver 320, image capture circuitry 330, video-based heart rate measurement module 340, and data collection module 305.

Wireless radios 315*a-n* comprise multiple radio interfaces required to communicate wirelessly with the other parties involved in user verification. In an embodiment, wireless radios 315*a-n* may comprise a Bluetooth radio, an IEEE 802.11 "WiFi" radio, and/or multiple wireless radios that are compatible with various cellular telecommunications standards such as 4G LTE, WiMAX, UMTS, and multiple CDMA-based technologies. The Bluetooth radio may serve to connect electronic device 300 with physiological measurement device 350 via a wireless Bluetooth link, such as link 116 of FIG. 1, while the WiFi radio and/or the radios compatible with cellular telecommunications standards may serve to connect electronic device 300 with a CV server, such as CV server 150 of FIG. 1, via a network such as network 140 of FIG. 1.

Network interface 310 serves as the interface between wireless radios 315*a-n* and the processing circuitry of electronic device 300. Network interface 310 enables the signal that is received wirelessly by electronic device 300 from physiological measurement device 350 to be translated into data that is usable by electronic device 300 to perform the steps required for user verification. In an embodiment, network interface 310 may perform demodulation steps required to convert electromagnetic signals received by wireless radios 315*a-n* into digital data that can be handled by the other elements of electronic device 300, such as device measurement receiver 320.

Network interface 310 is also responsible for converting data received from elements of electronic device 300 into a signal that can be transmitted wirelessly to other parties via wireless radios 315*a-n*. In an embodiment, network interface 310 may receive digital data from any element in electronic device 300 and perform various processing and modulation procedures to convert the digital data into a format that is appropriate for transmission over wireless radios 315*a-n*. This may include error correction coding of a data stream, the conversion of that bitstream into a symbol stream using any number of schemes such as binary phase shift keying (BPSK), quadrature phase shift keying (QPSK), or M-symbol quadrature amplitude modulation (QAM), as well as modulation such as CDMA for cellular telecommunications standards such as UMTS or CDMA3000, orthogonal frequency division multiplexing (OFDM) for LTE or WiFi, and so on. In this way, network interface 310 acts as both an ingress and egress point for digital data into and out of the various processing elements of electronic device 300.

Device measurement receiver 320 interacts with network interface 310 to receive data transmitted to electronic device 300 by physiological measurement device 350. While the network interface 310 converts wireless signals received by wireless radios 315*a-n* into digital data suitable for use by electronic device 300, device measurement receiver 320 may interpret the digital data from network interface 310 into data interpretable for user verification processes. In an embodiment, device measurement receiver 320 may receive the digital data from network interface 310, determine what portion of the digital data is specifically received from physiological measurement device 350, and convert that data into a form suitable for user verification purposes. For example, device measurement receiver 320 may determine that portions of the digital data received from network interface 310 represent physiological measurement data, such as video-based physiological measurement data 122 depicted in FIG. 1, and convert those portions of data into a format suitable for use in user verification. In an embodiment, device measurement receiver 320 may convert portions of the digital data into BPM numbers.

In another embodiment, device measurement receiver 320 may convert portions of the digital data into timestamps representing the times when physiological measurement device 350 detects a heartbeat pulse. In yet another embodiment, device measurement receiver 320 may convert portions of the digital data into time measurements between adjacent heartbeat pulses with tens of milliseconds or millisecond accuracy. In yet another embodiment, device measurement receiver 320 may also interpret portions of the digital data received from network interface 310 for data generated by physiological measurement device 350 that are not used for user verification. This data may include blood pressure, blood-sugar levels, number of steps walked, etc. All data that is interpreted by device measurement receiver 320 may be stored in storage and memory 317 depending on the data storage needs as based on user preferences. Data that is eventually transmitted to a third party server, such as third party server 160, may be stored in storage and memory 317 until it can be transmitted to the third party server.

Image capture circuitry 330 is responsible for collecting image data from a camera lens on electronic device 300. Image capture circuitry 330 may collect single frames (i.e. photos), such as photo 126, or continuous video, such as video 128, from the camera lens on electronic device 300. In an embodiment, continuous video may be captured at different frame rates, measured in frames per second (fps), depending on the processing capabilities of electronic device 300 and the camera lens on electronic device 300, as well as the requirements for user verification. For example, to obtain tens of milliseconds accuracy, the frame rate captured by image capture circuitry 330 via the camera lens on electronic device 300 must be at least 100 fps, as this would lead to a granularity of 0.01 seconds or less.

Video-based physiological measurement module 340 is responsible for obtaining physiological measurement data from video captured by image capture circuitry 330. The physiological measurement data generated by video-based physiological measurement module 340 may be an embodiment of video-based physiological measurement data 122. In embodiments, video-based physiological measurement module 340 may implement any of a number of algorithms designed to obtain physiological measurements from video. For example, Eulerian video magnification as described above may be implemented in video-based physiological measurement module 340 to process video captured by image capture circuitry 330, to obtain timestamps of heartbeat pulses, beats per minute, or time between adjacent heartbeat pulses.

Data collection module 305 acts to organize the collection of data by electronic device 300 from the user and from physiological measurement device 350 to perform user verification. Data collection module 305 may be an embodiment of application 121 depicted in FIG. 1. In an embodiment, data collection module 305 is responsible for prompting the user of electronic device 300 to perform any actions necessary to perform user verification via a user interface on electronic device 300. In an embodiment, data collection module 305 is also responsible for interacting with image capture circuitry 330 and the camera lens to film video such as video 128, take a photo such as photo 126, and obtain an identity document photo such as identity document photo 124. In an embodiment, data collection module 305 may also interact with wireless radios 315*a-n* via network interface 310, device measurement receiver 320, image capture circuitry 330 and video-based heart rate measurement module 340.

Storage and memory 317 serves as long-term and temporary storage of data collected by electronic device 300 from either physiological measurement device 350 or the user of electronic device 300. In an embodiment, the storage and memory may include of solid state drives, hard disk drives, and random access memory (RAM).

Physiological measurement device 350 may be an embodiment of physiological measurement device 110 of FIG. 1. Physiological measurement device 350 comprises wireless radios 365*a-n*, network interface 360, statistics module 370, physiological sensors 380*a-n* and memory 390. Many of these elements function in a fashion similar to their counterparts in electronic device 300, but have fewer capabilities owing to the lower complexity of physiological measurement device 350.

Wireless radios 365*a-n* may comprise multiple radio interfaces required to communicate wirelessly with the other parties involved in user verification. In an embodiment, wireless radios 365*a-n* may comprise a Bluetooth radio and/or an IEEE 802.11 "WiFi" radio. In an embodiment, wireless radios 365*a-n* may also include wireless radios that are compatible with various cellular telecommunications standards such as 4G LTE, WiMAX, UMTS, and multiple CDMA-based technologies. The Bluetooth radio may serve to connect physiological measurement device 350 with electronic device 300 via a wireless Bluetooth link, such as link 116 of FIG. 1, while the WiFi radio and the radios compatible with cellular telecommunications standards may serve to connect physiological measurement device 350 with a CV server, such as CV server 150 of FIG. 1, or a third party server, such as third party server 160 of FIG. 1, via a network such as network 140 of FIG. 1.

Network interface 360 serves as the interface between wireless radios 365*a-n* and the processing circuitry of physiological measurement device 350. Network interface 360 enables the signal that is received wirelessly by physiological measurement device 350 to be translated into data that is usable by physiological measurement device 350 to perform the steps required for user verification. In an embodiment, network interface 350 may perform demodulation steps required to convert electromagnetic signals received by wireless radios 365*a-n* into digital data that can be handled by the other elements of electronic device 300 such as device measurement receiver 320.

Network interface 360 is also responsible for converting data received from statistics module 370 into a signal that can be transmitted wirelessly to other parties via wireless radios 365*a-n*. In an embodiment, network interface 360 may receive digital data from statistics module 370 and perform various processing and modulation procedures to convert the digital data into a format that is appropriate for transmission over wireless radios 365*a-n*. This may include error correction coding of a data stream, the conversion of that bitstream into a symbol stream using any number of schemes such as binary phase shift keying (BPSK), quadrature phase shift keying (QPSK), or M-symbol quadrature amplitude modulation (QAM), as well as modulation such as CDMA for cellular telecommunications standards such as UMTS or CDMA3000, orthogonal frequency division multiplexing (OFDM) for LTE or WiFi, and so on. In this way, network interface 360 acts as both an ingress and egress point for digital data into and out of the various processing elements of physiological measurement device 350.

Statistics module 370 takes raw data output from physiological sensors 380a-n and creates meaningful measurements from them, and also acts as the interface between physiological sensors 380a-n and network interface 360. Physiological sensors 380a-n are highly specific and low-complexity, outputting raw bitstreams that must be interpreted by processing circuitry on physiological measurement device 350. Statistics module 370 may be implemented in the processing circuitry of physiological measurement device 350 to convert those raw bitstreams into more usable data. For example, statistics module 370 may take indications of a heartbeat pulse from one of the physiological sensors 380a-n and create a corresponding timestamp indicating when that heartbeat pulse was received according to a clock on physiological measurement device 350. In another embodiment statistics module 370 may calculate BPM based on some overlapping window scheme as described above. In another embodiment it may calculate time between adjacent heartbeat pulses. In another embodiment still, statistics module 370 may produce statistics for blood-sugar level, blood pressure, number of steps walked, and other health metrics based on outputs from other physiological sensors 380a-n. These statistics may be stored in memory 390 until they can be transmitted to another party with greater capability for long-term storage. In another embodiment, statistics module 370 may simply store the raw outputs from physiological sensors 380a-n along with metadata to indicate timestamps and transmit these raw data via network interface 360 and wireless radios 365a-n to another party.

Physiological sensors 380a-n measure various health indicators produced by a human body. Depending on what indicator is being measured, physiological sensors 380a-n may take on many different forms. Multiple methods may exist. For measuring heart rate, a process called "photoplethysmography" (PPG) is used which measures the amount of light absorption that can be detected from some part of a human body, typically a wrist. Thus, a green light may be shone onto some part of the person's body, by, for example, a green light on the underside of a wrist-watch style device. Green light absorption is then measured, where quick increases in absorption are determined to indicate a heartbeat pulse. For measuring blood oxygen levels, a similar process called pulse oximetry is used, where the ratio of the red light measurement to the infrared light measurement is measured to determine blood oxygen levels. For movement based health indicators, such as number of steps taken, a combination of motion detectors and gyroscopes may be implemented on the device to detect undulations in the movement of physiological measurement device 350. For blood pressure, a cuff on a physiological measurement device may be implemented which works similar to a sphygmomanometer, the common blood pressure meter in which a cuff inflates around the upper arm.

In embodiments, the required apparatus, including lights, gyroscopes, motion detectors, cuffs, and so on, are implemented as physiological sensors 380a-n within physiological measurement device 350 to allow for the measurement of various health indicators. Physiological sensors 380a-n produce simple outputs that are then received by statistics module 370 to create more complex statistics, or simply to store the raw data into memory 390 to await transmission to another party such as electronic device 300 or a CV server such as CV server 150 or third party server such as third party server 160.

Memory 390 serves as long-term and temporary storage of data collected by physiological sensors 380a-n or the user of electronic device 300. In an embodiment, the storage and memory may include solid state memory, memory cards, random access memory (RAM), and the like.

Figure 4:
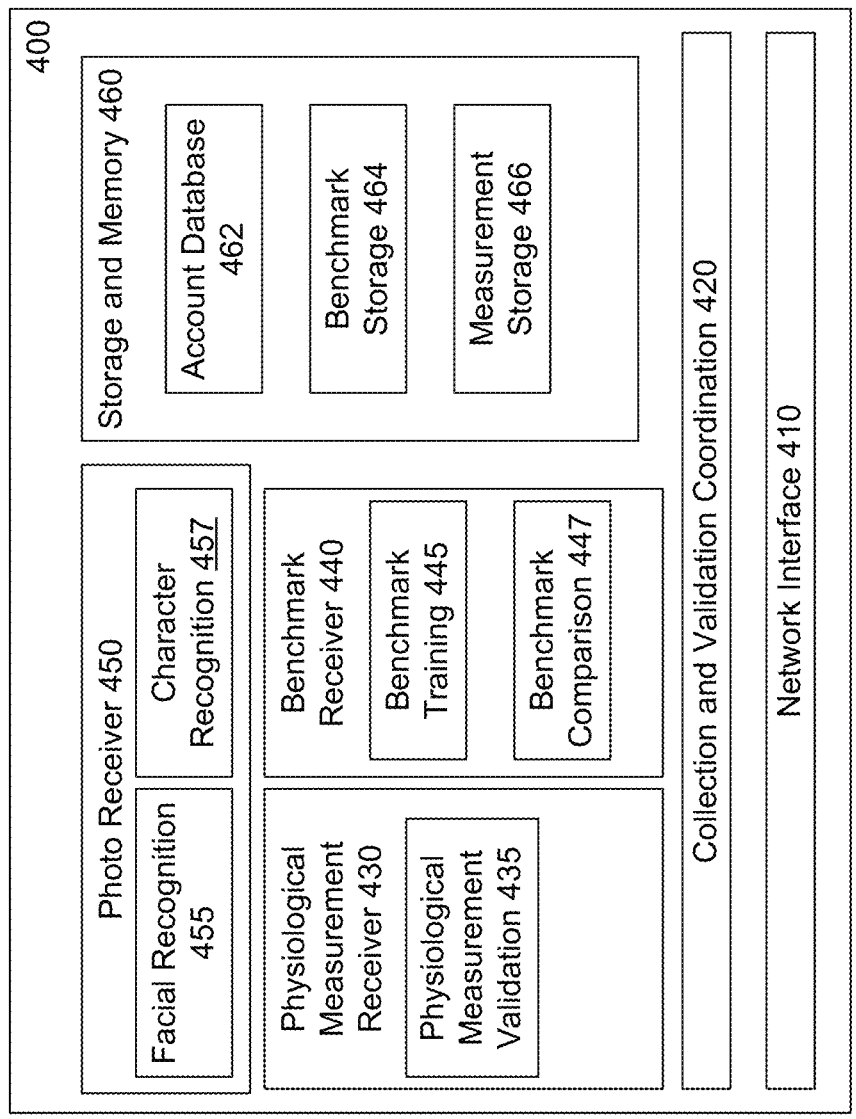
FIG. 4 illustrates a block diagram of a cloud-based server for user verification according to an embodiment.

FIG. 4 illustrates a CV server 400, according to an embodiment. CV server 400 may be an embodiment of CV server 150 depicted in FIG. 1. CV server may be implemented as a standalone server or server cluster owned by the provider of user verification services, or may be implemented virtually on any number of cloud services such as Amazon Web Services (AWS) or Google Cloud services. CV server 400 includes a network interface 410, a collection and validation (CV) coordinator 420, physiological measurement receiver 430 (including physiological measurement validation module 435), benchmark collection module 440 (including benchmark calculation module 445 and benchmark comparison module 447), photo receiver 450 (including facial recognition module 455 and text/character recognition module 457), and memory 460 (including an account database 462, benchmark storage database 464, and measurement storage 466). Each of these elements is described in detail below.

Network interface 410 serves as the interface between a network such as network 140 of FIG. 1 and the processing circuitry and elements of CV server 400. In an embodiment, network interface 410 may perform demodulation steps required to convert electromagnetic signals received from network 140 into digital data that can be handled by the various elements within CV server 400. CV server 400 may be connected a network via numerous landline networking standards such as IEEE 802.3 "Ethernet" protocol, and any demodulation steps required to receive signals over such landline standards may be implemented by network interface 410 to receive those signals and convert them to usable digital data. Network interface 410 is also responsible for performing any modulation required to transmit digital data formed within CV server 400 back to any of the other parties and devices depicted in FIG. 1. Therefore, digital data formed by, for example, physiological measurement validation module 435 may be converted into an electromagnetic signal that can be sent to a third party server such as third party server 160. In an embodiment network interface 410 is generally not linked to a wireless radio such as wireless radios 315a-n or 365a-n of FIG. 3. This is because CV server 400 is generally not linked directly to the wireless transmission hardware of a wireless service provider—a wireless service provider will act as a kind of middle man to receive bits wirelessly from electronic device 300 or physiological measurement device 350, convert them into electromagnetic signals appropriate for wireline communication, and send these along to network interface 410 of CV server 400.

CV coordinator 420 is responsible for receiving all data related to the user verification process and forwarding data to the receivers 450, 430, and 440 as necessary to perform the various steps in the user verification process. In an embodiment, for each step of the user verification process, CV coordinator 420 and a data collection module on an electronic device, such as data collection module 305 on electronic device 300, may perform a series of handshaking operations so that CV coordinator 420 knows what data is being sent by the electronic device at a given time. CV coordinator 420 can then forward photos to photo receiver 450, physiological measurement data to physiological measurement receiver 430, and benchmark data to benchmark receiver 440.

Photo receiver 450 may receive data representing photo images from network interface 410 via CV coordinator 420. In an embodiment, CV coordinator 420 may send photo data to photo receiver 450, and photo receiver 450 may perform any processing of the photo via facial recognition module 455 and character recognition module 457. In an embodiment, the character recognition module 457 may use OCR algorithms to extract legal information from a photo of an identity document, such as identity document photo 124. Facial recognition module 455 may also extract the facial features from a photo of a person's face, using any number of well-known techniques, from a photo of an identity document, such as identity document photo 124 and save these features to an appropriate file format for later use. The facial feature information along with the legal information extracted from a photo of an identity document may then be stored in account database 462 for later use. Both the facial feature information along with the legal information will be associated with an electronic device and a physiological measurement device, such that in subsequent user verifications, a selfie photo from the electronic device will be validated against the data associated with that electronic device.

This data may also be associated with an account for the owner of a third party server, such as third party server 160, which is offering a health incentive program. In an embodiment, such a photo of an identity document will be received during a user registration procedure with CV server 400 to engage in the health incentive program offered by the owner of a third party server such as third party server 160. As was described above, this owner may be an insurance company or a medical organization. Note that, in an embodiment, the identity document photo 124 must contain a photo of the person's face to be considered a valid document to be used for user verification. In other embodiments, identity document photo 124 may contain a picture of another location on the user.

In another embodiment, photo receiver 450 may receive a "selfie" photo of the face of a person using an electronic device, such as electronic device 300 or 120, during a different phase of user verification. Photo receiver 450 may send this photo to facial recognition module 455 to perform user verification by comparing the facial feature information from facial recognition module 455 with the identity-document based facial feature information for that user stored in account database 462. If the photos are determined not to match, photo receiver 450 may send an indicator to CV coordinator 420 that the match has failed. In an embodiment, CV coordinator 420 can send an indicator to an electronic device via network interface 410 to make another request for a selfie photo.

Once verifications are complete, data can be sent by photo receiver 450 to a third party server, such as third party server 160, or an electronic device, such as electronic device 300 or electronic device 120, via CV coordinator 420 and network interface 410. In an embodiment, following a user registration phase, the legal information and the facial feature information extracted from a photo on an identity document can be sent to the third party server. In another embodiment, data indicating the result of a comparison between a facial feature information from a selfie photo and the facial feature information from the corresponding identity document can be sent to the third party server.

Physiological measurement receiver 430 may receive two forms of physiological measurement data from CV coordinator 420 via network interface 410. In an embodiment, the two forms of physiological measurement data may be video-based physiological measurement data, such as video-based physiological measurement data 122, and physiological measurement data collected by a physiological measurement device, such as physiological measurement data 112. The physiological measurement data is received from an electronic device, such as electronic device 300 or 120, as part of a user verification process. The purpose of the two forms of physiological measurement data is to determine if the user of the electronic device is the same as the user of a physiological measurement device, such as physiological measurement device 350 or physiological measurement device 110. This relies on the fact that physiological measurement data from two different parties would be extremely unlikely to match when evaluated properly, and thus, if two sets of the same form of physiological measurement data are collected from an electronic device and a physiological measurement device in the same time interval, and both of these sets of physiological measurement data originate from the same person, they should match when evaluated based on a variety of criteria. For example, if the physiological measurement data from the physiological measurement device and the video-based physiological measurement data both include heart rate data, it is unlikely that the heart rate data over a given period of time would match if the two sets of data originated from two different people. In this example, if the heart rate data over a given period of time from both sets of data do match, then it is likely that both sets of data originate from the same person.

To that end, in an embodiment physiological measurement receiver 430 may send both physiological measurements to physiological measurement validation module 435 to determine if the physiological measurements match based on some criteria. Heart rate variability, for example, is a well-studied topic in the medical field. Depending on a variety of health factors, the time between adjacent heart beats, sometimes called a "beat-to-beat" interval, can vary widely. Heart rate variability analysis, therefore, may perform a variety of statistical analyses on the heart beat intervals. Frequency-domain methods such as fast Fourier transform are often performed to determine the power spectral density of the heart rate variability. Time-domain methods may be employed on heart beat intervals, such as determining the standard deviation, root mean square, standard deviation of successive differences, and so on.

In an embodiment, physiological measurement validation module 435 may produce a simple indicator that it has determined that the physiological measurements match. This indicator may be stored in storage and memory 460 in measurement storage database 466 or benchmark storage database 464. This indicator may be sent by physiological measurement receiver 430 to a third party server, such as third party server 160, via CV coordinator 420 and network interface 410. In another embodiment, physiological measurement validation module 435 may produce a probability between zero and one that the two physiological measurements match, and physiological measurement receiver 430 may send this probability to a third party server, such as third party server 160, via CV coordinator 420 and network interface 410. This probability may also be stored in storage and memory 460 in measurement storage database 466 or benchmark storage database 464.

In other embodiments, heart rate validation module 435 may determine that the physiological measurements do not match, or that the probability of the physiological measurements matching is below some threshold value. In such a case, an indicator of this determination may be sent to CV coordinator 420. In an embodiment, CV coordinator 420 may reinitiate a physiological measurement validation process by sending an indicator via network interface 410 to the electronic device that reported the mismatched physiological measurement data. In an embodiment, CV coordinator 420 may also determine, based on a history of past matching failures, that the user associated with the electronic device that is sending the physiological measurement data is not to be trusted, and may send an indication of this determination to the third party server. For example, if the number of failures over a given time window, such as a week or a month, is over some threshold, CV coordinator 420 may determine that this user cannot be trusted, send indications to third party server via network interface 410, and store that indicator in account database 462 such that it is linked with that user's identity document data within account database 462. Alternatively, CV coordinator 420 may send a probability of whether the user can be trusted, rather than making the final determination of whether the user can or cannot be trusted.

Benchmark receiver 440 may receive various health data, such as health data 114, to perform benchmark training. The purpose of benchmark training is to determine a set of metrics related to a user's health such that when data begins arriving from a physiological measurement device, such as physiological measurement device 350 or 110, CV server 400 may determine the likelihood that the data from the physiological measurement device represents the user associated with the physiological measurement device in account database 462.

To that end, following a successful user verification process where two forms of physiological measurement data are compared from an electronic device and physiological measurement device, such as electronic device 300 or 120 and physiological measurement device 350 or 110, CV coordinator 420 and an application on the electronic device may initiate a benchmarking process. In the benchmarking process, the user of the physiological measurement device continuously wears the device for some extended period of time. During this time, health data, such as health data 114, is continuously collected and reported to CV server 400 via network interface 410 and CV coordinator 420. CV coordinator sends this data to benchmark receiver 440, and benchmark training module 445 within benchmark receiver 440 uses various statistical and machine learning techniques to produce a model of the user's health and behavior. In embodiments, this model may include heart rate, blood pressure, blood sugar level, time of sleep and amount of sleep per day, common exercise times, at different times of day and different times of a given week. While the benchmark process is ongoing, benchmark training module 445 may continuously report and store new model data to benchmark storage database 464.

In another embodiment, after the benchmark process is complete, in subsequent sessions a physiological measurement device may begin reporting data that is received by CV server 400 via network interface 410 and CV coordinator 420. This data may also be health data such as health data 114. This data may be received by benchmark receiver 440 and this data may be sent to benchmark comparison module 447, which compares the newly received health data with the benchmark data stored in benchmark storage database 464. In an embodiment, benchmark comparison module 447 may report a probability that the health data received is indeed being produced by the customer associated with the physiological measurement device to a third party server via CV coordinator 420 and network interface 410.

As has been described above, storage and memory 460 stores the various data associated with the user verification processes executed by the elements of CV server 400, as well as an electronic device and physiological measurement device such as electronic device 300 and 120 and physiological measurement device 350 and 110. Storage and memory 460 comprises three databases: account database 462, benchmark storage database 464, and measurement storage database 466. As described above, in an embodiment account database 462 stores facial feature information and identity document information extracted from a photo of an identity document, such as identity document photo 124, as well as electronic device and physiological measurement device information associated with that information. This database creates these associations once an identity verification step has occurred that confirms that the user of the electronic device is indeed a customer of the third party offering a health incentive program. Benchmark storage database 464 stores the benchmark model data that is created by benchmark receiver 440 and benchmark training module 445 as described above. In other embodiments, measurement storage data 466 may store health data that is sent from the physiological measurement device during any of the user verification steps, benchmark training, or during regular reporting of data by the physiological measurement device for the health incentive program.

Methods for Verification

Figure 5:
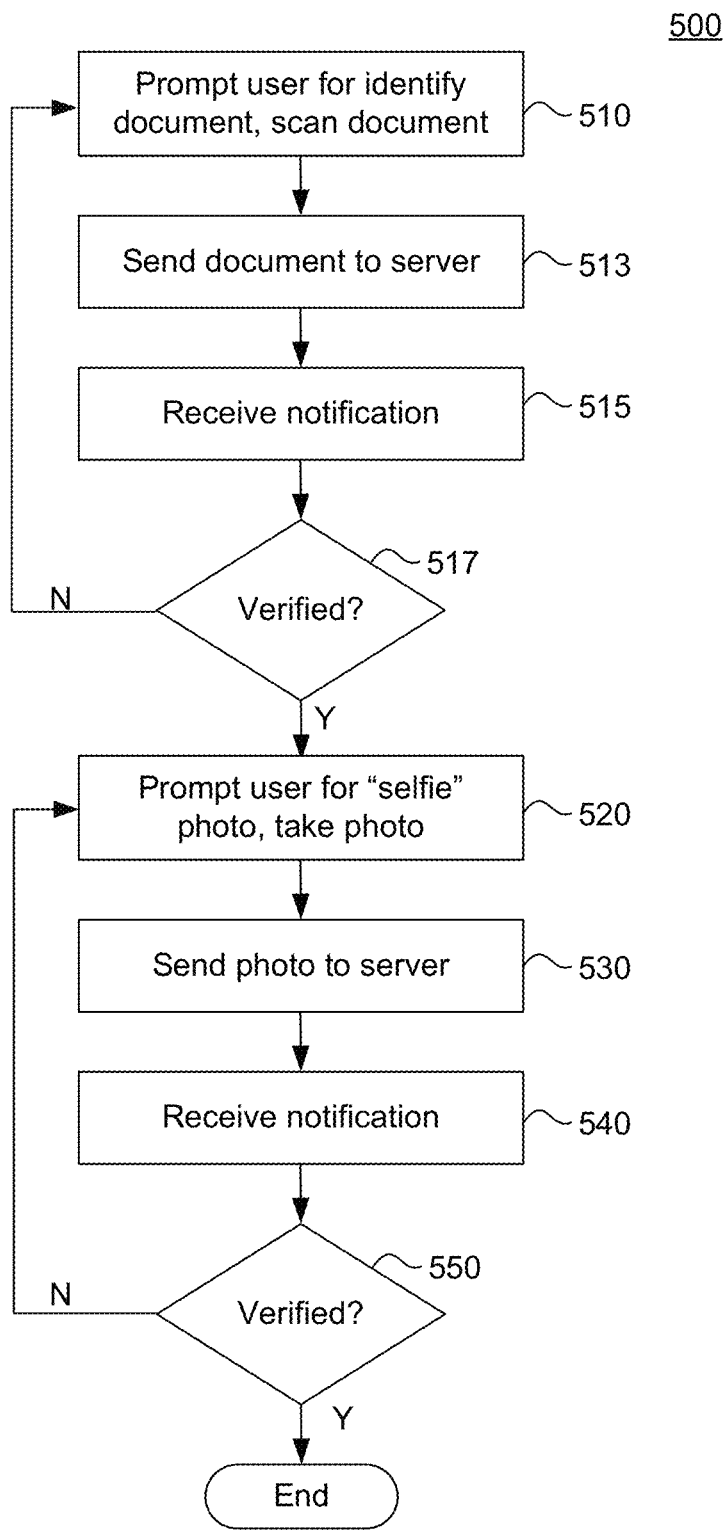
FIG. 5 illustrates a flowchart for identity verification according to an embodiment.

FIG. 5 illustrates flowchart 500 for an identity verification process according to an embodiment. Flowchart 500 corresponds to identity verification step 210 of FIG. 2. In an embodiment, an electronic device, such as electronic device 300 or 120, may perform the steps of flowchart 500. In step 510, an electronic device prompts a user of the electronic device to take a photo of an identity document. As was described above, the identity document may be a driver's license, passport, or other form of identity that has a photo of the user as well as legal information, such as the user's full name and date of birth. The user may then take a photo of the chosen identity document. In step 513, the electronic device sends the photo of the document to a CV server, such as CV server 150 or 400, to perform the steps necessary to extract information from the identity document. These steps will be described in greater detail with respect to FIG. 8A. In step 515, the electronic device receives a notification from the CV server that the identity document photo has been processed. If, in step 517, the notification indicates that identity document has been accepted by the CV server, then the electronic device progresses to step 520. If not, the electronic device may then prompt the user to take another photo of an identity document or request a different identity document.

In step 520, the user is prompted for a "selfie" photo. In an embodiment, this photo may be taken using a camera lens on the same face of the electronic device as the user interface (i.e. the screen), or may be taken with another lens as the user finds appropriate. After the photo is taken, in step 530 the selfie photo is sent to the CV server to perform the steps necessary to perform the comparison between the selfie photo and the face from the identity document photo. In step 540, the electronic device receives a notification from the CV server that the selfie photo has been processed. If, in step 550, the notification indicates that the selfie photo has been accepted by the CV server, then the identity verification process is completed and flowchart 500 ends. If not, the electronic device may then prompt the user to take another selfie photo to send to the CV server.

In embodiments, depending on the implementation of the identity verification process at the CV server, the entire process depicted by flowchart 500 may be restarted. For example, if a selfie photo is rejected a number of times over some threshold, the CV server may determine that the party initiating the identity verification process may not be trustworthy and start the process over at step 510.

Figure 6:
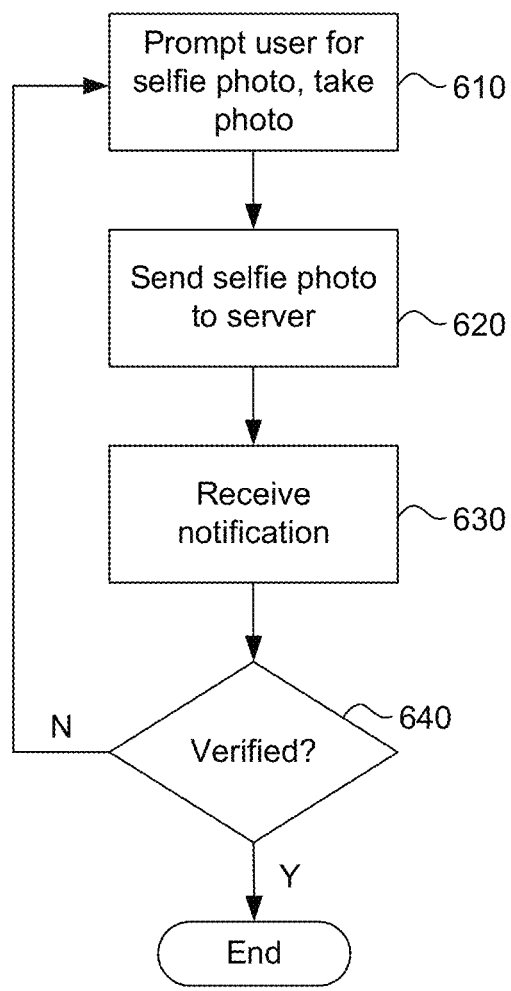
FIG. 6 illustrates a flowchart for user verification according to an embodiment.

FIG. 6 illustrates flowchart 600 for a user identification process according to an embodiment. Flowchart 600 corresponds to user verification step 220 of FIG. 2. In an embodiment, an electronic device, such as electronic device 300 or 120, may perform the steps of flowchart 600. As was described above, the user verification process, from the perspective of the electronic device, is similar to an abridged form of the identity verification process as depicted in flowchart 500. The user verification process depicted by flowchart 600 starts in step 610, where the electronic device prompts the user to take a selfie photo and the user does so. As was described above, this photo may be taken using a camera lens on the same face of the electronic device as the user interface (i.e. the screen), or may be taken with another lens as the user finds appropriate. After the photo is taken, in step 620 the selfie photo is sent to the CV server to perform the steps necessary to perform the comparison between the selfie photo and the face from the identity document photo. In step 630, the electronic device receives a notification from the CV server that the selfie photo has been processed. If, in step 640, the notification indicates that the selfie photo has been accepted by the CV server, then the identity verification process is completed and flowchart 600 ends. If not, the electronic device may then prompt the user to take another selfie photo to send to the CV server.

In embodiments, depending on the implementation of the user verification process at the CV server, if the user verification process depicted by flowchart 600 fails several times, the CV server may decide to reinitiate an identity verification process as depicted in flowchart 500. For example, if the CV server determines that the selfie photo received is rejected a number of times over some threshold, the CV server may determine that the party initiating the user verification process depicted by flowchart 600 is untrustworthy and that the customer account associated with the electronic device has been compromised. Therefore, the CV server may then send an instruction to the electronic device to reinitiate an identity verification process as depicted in flowchart 500 wherein the user may be prompted send a fresh photo of an identity document, as in step 510 of flowchart 500.

Figure 7:
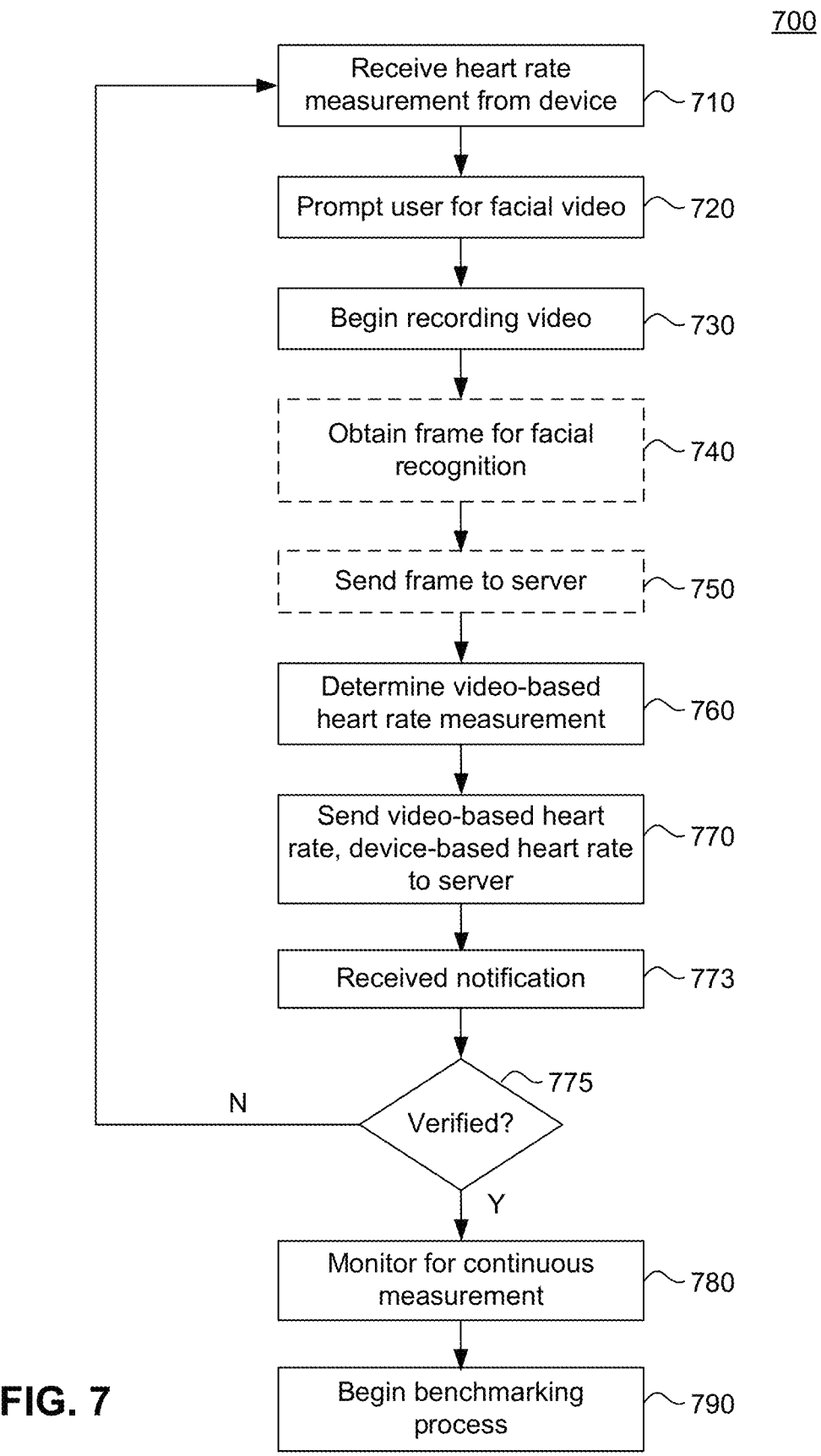
FIG. 7 illustrates a flowchart for user data collection and verification according to an embodiment.

FIG. 7 illustrates a flowchart 700 for performing heart rate matching comparison prior to a benchmark training process. Flowchart 700 corresponds to physiological measurement matching step 230 of FIG. 2. In an embodiment, an electronic device, such as electronic device 300 or 120, may perform the steps of flowchart 700. While Flowchart 700 uses a set of heart rate measurements as a specific example of physiological measurement, one of skill in the art will recognize that many types of physiological measurements, such as RR intervals, pulse waveform measurements, or any other physiological measurement may similarly be used.

The heart rate measurement matching process depicted by flowchart 700 begins in step 710, where real-time heart rate data is received from a physiological measurement device. The physiological measurement device producing the heart rate data may be an embodiment of the physiological measurement device 350 or 110 depicted in FIG. 3 and FIG. 1 respectively. The heart rate data itself may be an embodiment of physiological measurement data 112 depicted in FIG. 1. The heart rate data, as was described above, may be in the form of a series of BPM measurements, timestamps indicating the time of a heartbeat pulse, time between adjacent pulses, and so on. In an embodiment, the electronic device may send a message to the physiological measurement device to prompt the physiological measurement device to send the heart rate data. In another embodiment, the physiological measurement device may already be paired to the electronic device previously and be continuously reporting heart rate data as part of its regular function.

Simultaneously, in step 720, the electronic device may prompt the user to begin a facial "selfie video", a video trained on the user's face. In step 730, the user may press a button on the user interface of the electronic device to begin the recording of the video. If, during step 730, the video becomes unsuitable because of a severe change in the filming environment or because the video is no longer trained on the user's face, the filming may restart or the electronic device may simply move back to step 720 to again prompt the user to take video. Optionally, in step 740, a frame from the video may be taken to serve as a selfie photo to perform another user verification process as depicted in flowchart 600 of FIG. 6. In optional step 750, this frame may be sent to a CV server, such as CV server 400 or 150, whilst the video of the user's face is still being recorded.

In step 760, the electronic device may initiate the process of determining heart rate data based on the video shot in step 730. As was described above, many techniques exist for determining heart rate based on video, such as Eulerian video magnification. This heart rate data may be an embodiment of video-based physiological measurement data 122 depicted in FIG. 1. As was described above, the heart rate data generated in step 760 may be in the form of a series of BPM measurements, timestamps indicating the time of a heartbeat pulse, time between adjacent pulses, and so on.

At step 770, the video-based heart rate data generated in step 770, as well as the heart rate data that is received from the physiological measurement device in step 710, is sent to a CV server, such as CV server 400 or 150 for comparison. In an embodiment, the electronic device may determine matching time intervals of the heart rate data being reported such that the time window of the heart rate data from the physiological measurement device and the time window of the video-based heart rate data are the same at the CV server, thus reducing processing time at the CV server. In another embodiment, the heart rate data may simply be sent in a raw format to the CV server, where the CV server may handle the various formatting issues of the two heart rate data types.

In step 773, a notification may be received from the CV server indicating the result of the comparison of the heart rate data by the CV server from the heart rate data sent by the electronic device to the CV server in step 770. In step 775, if the notification indicates that the heart rate data are determined to match, the process may move on to optional step 780. If not, the process may reset to step 710 to restart collection of heart rate data from video and from the physiological measurement device.

In optional step 780, the electronic device may monitor to ensure that the physiological measurement device is obtaining continuous health data metrics from the user of the device. This step is designed to ensure that the user of the physiological measurement device does not change between the heart rate verification steps 710-775 and the benchmarking process. In step 790, the electronic device may receive a notification from the CV server to begin collecting measurements from the physiological measurement device to perform benchmark training. The benchmark training may be an embodiment of benchmark training step 240 of FIG. 2.

FIGS. 8A-B illustrate flowcharts 800 and 850 for performing an identity verification process according to an embodiment. Flowcharts 800 and 850 correspond to identity verification step 210 of FIG. 2. In an embodiment, a CV server, such as CV server 400 or CV server 150, may perform the steps of flowcharts 800 and 850. Flowchart 800 begins in step 810, where a photo of an identity document is received from an electronic device such as electronic device 300 or 120. This corresponds to step 513 of FIG. 5, where the electronic device sends an identity document photo. The identity document photo may be an embodiment of identity document photo 124 of FIG. 1. A CV coordinator, such as CV coordinator 420 of CV server 400, may receive the identity document photo.

In step 813, the CV server performs a check to determine if the identity document contains a photo of the user. If not, a notification is sent in step 833 to the electronic device that the identity document does not match a record of a customer of the third party, and the CV server goes back to waiting to receive an identity document in step 810. If it does contain a photo of the user, then the process moves on to character recognition step 815.

In step 815, a character recognition process is performed on the identity document received in step 810. This may be performed by a character recognition module, such as character recognition module 457. In embodiments, this character recognition will extract some combination of legal information, such as legal name, date of birth, address, city and so on from the identity document.

In step 820, the legal information determined in step 815 is checked to see if it matches a customer of the third party offering the health incentive program. In an embodiment, the CV server may have customer information from the third party stored locally, and the CV server can perform simple string matching to determine if the legal information matches a customer's information from the third party. In another embodiment, the CV server may send the legal information to the third party server, such as third party server 160, and the third party server can determine if the legal information matches one of their customers, and can send an indication back to the CV server as to whether or not a match is found. In step 830, if a match is determined to exist, flowchart 800 moves on to step 835. If not, then in step 833, a notification is sent to the electronic device that the identity document does not match or has a low probability of matching a record of a customer of the third party, and the CV server goes back to waiting to receive an identity document in step 810. Additionally or alternatively, the CV server may send a notification to the third party server that the identity document does not match, or a probability of match that the third party can use to make its own determination.

In step 835, after a match is determined to exist, the CV server sends a notification to the electronic device that the identity document does match or has a high probability of matching a customer of the third party. Additionally or alternatively, the CV server may send a notification to the third party server that the identity document matches, or a probability of match that the third party can use to make its own determination. Then in step 840, the CV server then goes on to perform facial recognition on the photo of the user within the photo identity document. Step 840 may be performed by a facial recognition module such as facial recognition module 455. This facial recognition will produce facial feature information which is used as baseline criteria for later verification steps.

FIG. 8B depicts flowchart 850, a second part of the identity verification process, according to an embodiment. In step 860, the CV server may receive a selfie photo from the electronic device. In step 865, facial recognition is then performed on the selfie photo received in step 860. In an embodiment, the algorithm used for facial recognition may be the same as the algorithm used for facial recognition in step 850 for the photo appearing in the identity document received as part of flowchart 800. In step 870, the CV server may then perform a comparison between the facial features data obtained in step 870 with the facial feature information obtained in step 850 from facial recognition of the user's photo in the identity document. If a match is determined in step 880, CV server then performs step 885. If not, a notification is sent in step 882 to the electronic device and the CV server returns to step 860 to wait to receive a selfie from the electronic device. Additionally or alternatively, the CV server may send a notification to the third party server that the facial feature data does not match, or a probability of match that the third party can use to make its own determination.

In step 885, the CV server has now determined that a valid identity document has been sent with legal information and a user photo, and that the user of the electronic device is indeed the same as the person that appears in the identity document. At this point, the identity of the user has now been verified, and the CV server can now create an account for the user so that the user may begin to participate in a health incentive program offered by the third party. In an embodiment, an account record will aggregate the legal information obtained from the legal document, the customer information from the third party, the facial feature information from the user's photo from the identity document, and information relating to the electronic device used by the user. In another embodiment, the physiological measurement device that the user wishes to use to participate in the health incentive program may also be noted in the account record. Alternatively, the CV server may send a notification to the third party server that the user has been verified, or a probability that the user is valid, that the third party can then use to make its own determination. The third party server may then create an account for the user so that the user may begin to participate in a health incentive program offered by the third party.

In step 890, the CV server will send a notification to the electronic device indicating that the account has been created. This concludes the identity verification process.

FIG. 9 illustrates flowchart 900 for performing a user verification process according to an embodiment. Flowchart 900 corresponds to identity verification step 220 of FIG. 2. In an embodiment, a CV server, such as CV server 400 or CV server 150, may perform the steps of flowchart 900. As was described above, the user verification process is essentially an abridged form of the identity verification process, where the identity document data has already been stored and all that is required is the selfie comparison to the user photo from the identity document.

In step 910, the CV server receives a selfie photo from an electronic device such as electronic device 300 or 120. In an embodiment, the photo may be accompanied by account identifier information from the electronic device such that the CV server knows which account the user of the electronic device wishes to access to participate in the health incentive program. In step 920, facial recognition is performed on the received selfie photo, and the determined facial feature information from the selfie photo is compared to the facial feature information of the user photo from the identity document. In an embodiment, the same facial recognition algorithm used to determine the facial feature information from the user photo of the identity document is used on the selfie received in step 910.

If, in step 930, the selfie is determined to be a photo of the same user as the user photo from the identity document, and in step 940 a notification is sent to the electronic device and the process ends. If not, then in step 935, a notification indicating that the person in the selfie photo does not match the person in the identity document is sent to the electronic device and the CV server goes back to step 910 to await a new selfie photo from the electronic device. Additionally or alternatively, the CV server may send a notification to the third party server that the photos do not match, or a probability of match that the third party can use to make its own determination.

FIG. 10 illustrates flowchart 1000 for performing a physiological measurement matching procedure according to an embodiment. Flowchart 1000 corresponds to identity verification step 210 of FIG. 2. In an embodiment, a CV server, such as CV server 400 or CV server 150, may perform the steps of flowchart 1000. The process starts in step 1010, where the CV server receives two sets of physiological measurements from an electronic device such as electronic device 300 or 120. Each set of physiological measurements may be, for example, a set of sequential physiological measurements. The two sets of physiological measurements correspond to physiological measurement data collected by a physiological measurement device such as physiological measurement device 350 or 110 and video-based physiological measurement data produced by the electronic device. These two sets of physiological measurements may be embodiments of physiological measurement data 112 and video-based physiological measurement data 122 depicted in FIG. 1. As was described above, both sets of physiological measurements may be in the form of a series of BPM measurements based on overlapping time windows, timestamps indicating the time of a heartbeat pulse, time between adjacent pulses, and so on.

In step 1020, the CV server may perform a comparison between the two sets of physiological measurements. This step may be performed by a physiological measurement validation module within the CV server, such as physiological measurement validation module 435 depicted in FIG. 4. Depending on the form of physiological measurements received by the electronic device, this comparison may take different forms. In an embodiment, the two sets of physiological measurements may be BPM measurements from overlapping time windows, and the CV server may simply compare BPM measurements from the same time windows from each of the heart rate measurements and determine a likelihood that they are from the same party based on the similarity of those BPM measurements. In another embodiment, the sets of physiological measurements may be timestamps of heartbeat pulses, and the CV server may determine a likelihood that they are from the same party based on how close the timestamps are to each other within some given larger time window. In another embodiment, the sets of physiological measurements may be times between adjacent heartbeat pulses and the CV server may compare the times between the different heart rate measurements, or perform some form of statistical analysis to determine if the heart rate variability of the two heart rate measurements is sufficiently similar.

If, in step 1030, if the two sets of physiological measurements are determined to be sufficiently similar, CV server moves to step 1040. If not, CV server sends a notification to the electronic device in step 1035 that the two sets of physiological measurements are determined to not be from the same source and the CV server goes back to waiting to receive two sets of physiological measurements in step 1010. Additionally or alternatively, the CV server may send a notification to the third party server that the two sets of physiological measurements are determined to not be from the same source, or a probability that the third party can use to make its own determination. In an embodiment, if the physiological measurement comparison fails a number of times over some threshold, the CV server may then ask the user of the electronic device to perform identity verification or user verification again, such as steps 210 or 220 of FIG. 2.

If the two sets of physiological measurements are determined to be sufficiently similar, CV server in step 1040 sends the electronic device a notification that the CV server has deemed the heart rate measurements acceptable. Additionally or alternatively, the CV server may send a notification to the third party server that the two sets of physiological measurements are determined to be sufficiently similar, or a probability of similarity that the third party can use to make its own determination of acceptability. At this point, the CV server may move to optional step 1050, wherein the CV server may receive measurements of benchmark training. As was described above, during benchmark training health data of various kinds may be received by the CV server from a physiological measurement device via the electronic device, and the CV server may perform various statistical and machine learning techniques to produce a model of the user's health and behavior. This model can then be used when the user sends new data to the CV server or third party server when participating in the health incentive program and the CV server may evaluate a probability that this new data is trustworthy in reflecting the various health metrics of the customer of the third party.

Computer System

It will be apparent to persons skilled in the relevant art(s) that various modules and features of the present disclosure, as described herein, can be implemented in hardware using analog and/or digital circuits, in software, through the execution of computer instructions by one or more general purpose or special-purpose processors, or as a combination of hardware and software.

Embodiments of the present disclosure can be implemented in hardware, or as a combination of software and hardware. Consequently, embodiments of the disclosure may be implemented in the environment of a computer system or other processing system. For example, CV server 400 depicted in FIG. 4 and its associated operational flows depicted in FIGS. 8A-B, 9 and 10 can be implemented in the environment of one or more computer systems or other processing systems. An example of such a computer system 1100 is shown in FIG. 11.

FIG. 11 illustrates an exemplary embodiment of a computer system 1100 that can be used to implement the methods and apparatus of the present invention. Computer system 1100 includes one or more processors, such as processor 1104. Processor 1104 can be a special purpose or a general purpose digital signal processor. Processor 1104 is connected to a communication infrastructure 1106 (for example, a bus or network). Various software implementations are described in terms of this exemplary computer system. After reading this description, it will become apparent to a person skilled in the relevant art(s) how to implement the disclosure using other computer systems and/or computer architectures.

Computer system 1100 also includes a main memory 1108, preferably random access memory (RAM), and may also include a secondary memory 1130. Secondary memory 1130 may include, for example, a hard disk drive 1112 and/or a removable storage drive 1114, representing a floppy disk drive, a magnetic tape drive, an optical disk drive, or the like. Removable storage drive 1114 reads from and/or writes to a removable storage unit 1118 in a well-known manner. Removable storage unit 1118 represents a floppy disk, magnetic tape, optical disk, or the like, which is read by and written to by removable storage drive 1114. As will be appreciated by persons skilled in the relevant art(s), removable storage unit 1118 includes a computer usable storage medium having stored therein computer software and/or data.

In alternative implementations, secondary memory 1130 may include other similar means for allowing computer programs or other instructions to be loaded into computer system 1100. Such means may include, for example, a removable storage unit 1122 and an interface 1120. Examples of such means may include a program cartridge and cartridge interface (such as that found in video game devices), a removable memory chip (such as an EPROM, or PROM) and associated socket, a thumb drive and USB port, and other removable storage units 1122 and interface 1120 which allow software and data to be transferred from removable storage unit 1122 to computer system 1100.

Computer system 1100 may also include a communications interface 1124. Communications interface 1124 allows software and data to be transferred between computer system 1100 and external devices. Examples of communications interface 1124 may include a modem, a network interface (such as an Ethernet card), a communications port, a PCMCIA slot and card, etc. Software and data transferred via communications interface 1124 are in the form of signals which may be electronic, electromagnetic, optical, or other signals capable of being received by communications interface 1124. These signals are provided to communications interface 1124 via a communications path 1126. Communications path 1126 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 1118 and 1122 or a hard disk installed in hard disk drive 1112. These computer program products are means for providing software to computer system 1100.

Computer programs (also called computer control logic) are stored in main memory 1108 and/or secondary memory 1130. Computer programs may also be received via communications interface 1124. Such computer programs, when executed, enable the computer system 1100 to implement the present disclosure as discussed herein. In particular, the computer programs, when executed, enable processor 1104 to implement the processes of the present disclosure, such as any of the methods described herein. Accordingly, such computer programs represent controllers of the computer system 1100. Where the disclosure is implemented using software, the software may be stored in a computer program product and loaded into computer system 1100 using removable storage drive 1114, interface 1120, or communications interface 1124.

In another embodiment, features of the disclosure are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

What is claimed is:

1. A system for verifying physiological data of a user for use by a third party, the system comprising:
   a. a physiological measurement device associated with the user, the physiological measurement device comprising:
      physiological sensors;
      processing circuitry configured to take raw output from the physiological sensors and create the physiological data of the user, the physiological data of the user comprising a first set of physiological measurement data of the user and a corresponding first set of timestamps; and
      a physiological measurement device network interface;
   b. an electronic device associated with the user, the electronic device comprising:
      an electronic device network interface;
      a camera lens; and
      processing circuitry configured to:
         capture image data from the camera lens, wherein image data comprises a photo of a face of the user and a video of the user, the photo taken concurrently with the video;
         create a second set of physiological measurement data from captured image data of the associated user and a corresponding second set of timestamps;
         receive the physiological data, including the first set of physiological measurement data and corresponding first set of timestamps, from the physiological measurement device network interface via the electronic device network interface; and
         send the physiological data, including the first set of physiological measurement data and corresponding timestamps, and the second set of physiological measurement data and second set of corresponding timestamps to a server via the electronic device network interface; and
   c. the server comprising:
      memory that stores identity facial feature information of a registered user associated with the physiological measurement device and the electronic device;
      a server network interface configured to communicate with the electronic device network interface; and
      one or more processors, coupled to the server network interface and the memory, configured to:
         receive, from the electronic device, the photo of the face of the user of the electronic device;
         process the photo of the face to obtain facial feature information of the user of the electronic device using facial recognition;
         determine that the facial feature information of the user of the electronic device matches the identity facial feature information of the registered user to verify the user of the electronic device is the registered user using facial recognition; and
         in response to determining that the facial feature information of the user of the electronic device matches the identity facial feature information of the registered user:

receive, from the electronic device, the physiological data, including the first set of physiological measurement data and corresponding timestamps, the second set of physiological measurement data, and the second set of corresponding timestamps;

determine that the first set of physiological measurement data from the user of the physiological measurement device and the second set of physiological measurement data from the electronic device user are matching based on a matching criteria to verify the physiological measurement device user is the electronic device user by comparing the first set of physiological measurement data and the corresponding timestamps match the second set of physiological measurement data and the second set of corresponding timestamps; and in response to the determining that the first set of physiological measurement data and the second set of physiological measurement data are matching, send the first set of physiological measurement data and a notification to the third party server that the first set of physiological measurement data matches the second set of physiological measurement data to verify the physiological measurement device user and the electronic device user are the registered user, wherein the system is configured to perform the verification whenever the server requests the physiological data of the user.

2. The verification system of claim 1, wherein the second set of physiological measurement data from the electronic device user is generated by the electronic device using Eulerian video magnification from the video of the electronic device user.

3. The verification system of claim 1, wherein the one or more processors of the server is further configured to:
receive an identity document photo associated with the electronic device user from the electronic device, the identity document photo including text information and an identity photo; and
process the identity document photo to generate legal information based on the text information and the identity facial feature information based on the identity photo.

4. The verification system of claim 3, wherein the one or more processors of the server is further configured to:
determine that the legal information processed from the identity document photo received from the electronic device matches customer information of the registered user, wherein the customer information of the registered user is associated with the third party server.

5. The verification system of claim 4, wherein to determine that the legal information matches the customer information of the registered user, the one or more processors of the server is further configured to:
send the legal information to the third party server; and
receive, from the third party server, a second notification indicating that the legal information matches the customer information of the registered user stored in the third party server.

6. The verification system of claim 4, wherein in response to determining that the facial feature information matches the identity facial feature information of the registered user, the one or more processors of the server is further configured to:
create account information including the identity facial feature information and the customer information; and
store the account information in the memory.

7. The verification system of claim 1, wherein in response to the determining that the first set of physiological measurement data from the physiological device user and the second set of physiological measurement data from the electronic device user are matching, the one or more processors of the server is further configured to:
receive health data from the electronic device, wherein the health data is generated by the physiological measurement device; and
create a health model based on the health data.

8. A method for confirming that a registered user is operating an electronic device and a physiological measurement device, comprising:
receiving, from the electronic device, a photo of a face of the user of the electronic device captured by camera lens of the electronic device;
processing the photo of the face to obtain facial feature information of the user of the electronic device;
determining that the facial feature information of the electronic device user matches identity facial feature information of the registered user using facial recognition; and
in response to determining that the facial feature information of the electronic device user matches the identity facial feature information of the registered user:
receiving, from the electronic device, a signal including a first set of physiological measurement data, a corresponding first set of timestamps, a second set of physiological measurement data, and a corresponding second set of timestamps, wherein the first set of physiological measurement data is generated by the physiological measurement device for a user of the physiological measurement device, the second set of physiological measurement data is generated by the electronic device from video captured by the camera lens of the electronic device for the electronic device user, and the corresponding first and second sets of timestamps are generated by the electronic device;
determining that the first set of physiological measurement data of the physiological measurement device user and the second set of physiological measurement data of the electronic device user are matching based on a matching criteria utilizing the corresponding first and second set of timestamps; and
in response to the determining that the first set of physiological measurement data and the second set of physiological measurement data are matching, sending the first set of physiological measurement data and a notification to a third party server that the first set of physiological measurement data matches the second set of physiological measurement data to verify the physiological measurement device user and the electronic device user are the registered user so the third party server can link to the register user, and utilize the first set of physiological measurement data.

9. The method of claim 8, wherein the second set of physiological measurement data is generated by the electronic device based on a video of the face of the electronic device user, and the photo of the face is a frame from within the video of the face.

10. The method of claim 9, wherein the second set of physiological measurement data is generated by the electronic device using Eulerian video magnification on the video of the face of the electronic device user.

11. The method of claim 8, further comprising:
receiving an identity document photo associated with the electronic device user from and captured by the camera lens of the electronic device, the identity document photo including text information and an identity photo; and
processing the identity document photo to generate legal information based on the text information and the identity facial feature information based on the identity photo.

12. The method of claim 11, further comprising:
determining that the legal information processed from the identity document photo captured by the electronic device matches customer information of the registered user, wherein the customer information of the registered user is associated with the third party server.

13. The method of claim 12, wherein the determining that the legal information of the electronic device matches the customer information of the registered user further comprises:
sending the legal information to the third party server; and
receiving, from the third party server, a second notification indicating that the legal information from the electronic device user matches the customer information of the registered user stored in the third party server.

14. The method of claim 12, further comprising, in response to determining that the facial feature information processed from the photo captured by the electronic device user matches identity facial feature information of the registered user, creating account information including the identity facial feature information and the customer information.

15. A system for verification of a user of a physiological measurement device, comprising:
the physiological measurement device associated with the user comprising:
physiological sensors; and
processing circuitry configured to take raw output from the physiological sensors and create physiological data of the user, the physiological data comprising a first set of heart rate data of the user of the physiological measurement device;
an electronic device associated with a user, configured to:
receive the physiological data of the user, including the first set of heart rate data, from the physiological measurement device via a wireless link;
record a video of a face of the electronic device user via image capture circuitry on the electronic device, while the physiological measurement device is creating the first set of heart rate data, wherein the electronic device is configured to generate a photo of the electronic device user from the video;
generate a second set of heart rate data associated with the electronic device user based on the video using Eulerian video magnification from the video of the face of the electronic device user;
transmit the photo and the physiological data of the user, including the first set of heart rate physiological data associated with the physiological measurement device, and the second set of heart rate data associated with the electronic device user to a collection and validation (CV) server via a second wireless link; and
the CV server, configured to:
confirm the user of the electronic device is a registered user of a third party server by matching identity facial feature information of the registered user using facial recognition algorithms;
receive the physiological data, including the first set of heart rate data, and the second set of heart rate data from the electronic device;
determine that the first set of heart rate data and the second set of heart rate data, both the first set and second set captured at the same time, are matching based on a matching criteria to verify the physiological measurement device user is the electronic device user;
in response to the determining that the first set of heart rate data and the second set of heart rate data are matching, sending a notification to the third party server that the first set of physiological measurement data matches the second set of physiological measurement data, verifying the physiological measurement device user is the electronic device user; and
send the physiological data from the physiological measurement device associated with the user to the third party server for use in a health insurance benefit program.

16. The system of claim 15, wherein the electronic device is further configured to:
capture an identity document photo associated with the electronic device user, the identity document photo including text information and an identity photo; and
transmit the identity document photo to the CV server;
wherein the CV server is further configured to:
receive the identity document photo of the electronic device user from the electronic device; and
process the identity document photo to generate legal information based on the text information and identity facial feature information based on the identity photo of the electronic device user.

17. The system of claim 16, wherein the electronic device is further configured to:
capture a photo of the face of the electronic device user; and
transmit the photo to the CV server;
wherein the CV server is further configured to, before receiving the first set of physiological measurement data and the second set of physiological measurement data:
receive the photo of the face of the electronic device user from the electronic device;
process the photo of the face of the electronic device user to generate facial feature information; and
determine that the facial feature information from the photo matches identity facial feature information from the identity document photo using facial recognition.

18. The system of claim 16, wherein the CV server is further configured to determine that the legal information from the identity document photo matches customer information of a registered user, wherein the customer information of the registered user is associated with the third party server whom with the registered user has registered.

19. The system of claim 1, wherein the first and the second set of physiological measurement data comprise heart rate measurements.

* * * * *